US012761162B2

(12) United States Patent
Khan et al.

(10) Patent No.: US 12,761,162 B2
(45) Date of Patent: Oct. 13, 2026

(54) CONTACTLESS SOIL MOISTURE ESTIMATION USING RADIOFREQUENCY SIGNALS

(71) Applicant: North Carolina State University, Raleigh, NC (US)

(72) Inventors: Usman Mahmood Khan, Raleigh, NC (US); Muhammad Shahzad, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 235 days.

(21) Appl. No.: 18/444,190

(22) Filed: Feb. 16, 2024

(65) Prior Publication Data

US 2024/0280510 A1 Aug. 22, 2024

Related U.S. Application Data

(60) Provisional application No. 63/485,592, filed on Feb. 17, 2023.

(51) Int. Cl.
*G01N 22/04* (2006.01)
*G01N 33/24* (2006.01)

(52) U.S. Cl.
CPC ........... *G01N 22/04* (2013.01); *G01N 33/246* (2013.01); *G01N 33/245* (2024.05)

(58) Field of Classification Search
CPC ........ G01N 22/04; G01N 27/02; G01N 27/04; G01N 27/22; G01N 33/24; G01N 33/246;
(Continued)

(56) References Cited

U.S. PATENT DOCUMENTS 6,496,137 B1 * 12/2002 Johansson ................ G01V 3/12 342/22
2007/0235250 A1 * 10/2007 Krumhansl ............ G01V 1/047 181/121

(Continued)

FOREIGN PATENT DOCUMENTS

GB 2595726 A * 12/2021 ......... H04Q 11/0005

OTHER PUBLICATIONS

United States Environmental Protection Agency. Water Sense. Statistics and Facts. Updated 20024. https://www.epa.gov/watersense/statistics-and-facts.

(Continued)

*Primary Examiner* — Lee E Rodak
*Assistant Examiner* — Taqi R Nasir
(74) *Attorney, Agent, or Firm* — Meunier Carlin & Curfman LLC

(57) ABSTRACT

A system for estimating moisture in soil includes a first antenna for transmitting RF signals, second antennas for receiving RF signals, and a controller configured to: emit, via the first antenna, RF signals at a plurality of frequency increments; determine a channel frequency response (CFR) based on amplitude attenuation and phase change of reflected RF signals detected by the second antennas; determine a power delay profile (PDP) for the second antennas based on the CFRs; extract a subset of the reflected RF signals using peak detection on the PDPs; and for each layer of the soil and for each of the subset of reflected RF signals, determine: i) a wavelength of the reflected RF signal in the layer, ii) an estimated depth of the layer, iii) a dielectric permittivity of the layer based on the wavelength, and iv) an estimated moisture content of the layer based on the dielectric permittivity.

20 Claims, 11 Drawing Sheets

(58) Field of Classification Search
CPC ...... G01N 33/245; G01R 27/04; G01R 27/26; G01R 25/00; G01R 23/16
USPC ................ 324/609, 658, 636, 601, 707, 637
See application file for complete search history.

(56) References Cited

U.S. PATENT DOCUMENTS

| | | | | |
|---|---|---|---|---|
| 2015/0268218 | A1* | 9/2015 | Troxler | G01S 13/885 342/21 |
| 2021/0248488 | A1* | 8/2021 | Naseef | H04W 24/02 |
| 2022/0224583 | A1* | 7/2022 | Rosenthal | H04L 27/02 |

OTHER PUBLICATIONS

Comet-moisture. https://gitfront.io/r/user-1279687/dfb6d2fb4bcc945dcdfdef117c9812d036682ac3/comet-moisture/.
TEROS 12. Advanced Soil Moisture Sensor + Temperature and EC. https://www.metergroup.com/environment/products/teros-12/.
Scale of Variable Measurement. https://www.stat.purdue.edu/~tqin/system101/variable_type.pdf.
5TE Manual https://envcoglobal.com/files/docs/5te-manual-08.pdf.
Ettus. X300/X310 https://kb.ettus.com/X300/X310.
Alfa APA-M25 https://www.alfa.com.tw/products/apa-m25.
Neewer Aluminum Alloy Camera Track Slider Video Stabilizer Rail with 4 Bearings for DSLR Camera DV Video Camcorder Film Photography, Loads up to 17.5 pounds/8 kilograms (60cm) https://www.amazon.com/Neewer-Centimeters-Stabilizer-Camcorder-Photography/dp/B06Y3MKC7C/.
Mast Technologies. MF22-0009-00. 2018. http://www.masttechnologies.com/wp-content/uploads/2019/02/MF22-0009-00-Tech-Data-Sheet.pdf.
A Practical Guide for Installing and Interpreting Information from Soil Moisture Monitoring Technologies in Vineyards. https://www.vineyardteam.org/resources/resource-library/usingsoil-moisture-sensors-for-vineyard-irrigation-management.php.
Soil moisture monitoring: a selection guide. https://www.agric.wa.gov.au/horticulture/soil-moisture-monitoring-selection-guide.
F Adib and et. al. 2014. 3D Tracking via Body Radio Reflections. In Usenix NSDI. Usenix Association, Seattle, WA, 317-329.
J. H Bradford. 2008. Measuring water content heterogeneity using multifold GPR with reflection tomography. Vadose Zone Journal 7 (2008), 184-193. https://doi.org/10.2136/vzj2006.0160.
E. A Colman. 1946. The place of electrical soil-moisture meters in hydrologic research. Eos, Transactions American Geophysical Union. 27, 6 (1946), 847-853.
M Cornick and et. al. 2016. Localizing Ground Penetrating Radar: A Step Toward Robust Autonomous Ground Vehicle Localization. Field Robotics 33 (2016), 82-102. https://doi.org/10.1002/rob.21605.
A Dhekne and et. al. 2018. LiquID: A Wireless Liquid IDentifier. In MobiSys. Association for Computing Machinery, New York, NY, USA, 442-454. https://doi.org/10.1145/3210240.3210345.
J Ding and R Chandra. 2019. Towards Low Cost Soil Sensing Using Wi-Fi. In Mobicom. 1-16. https://doi.org/10.1145/3300061.3345440.
M. D Dukes. 2020. Two decades of smart irrigation controllers in US landscape irrigation. Transactions of the ASABE 63 (2020), 1593-1601, Issue 5.
H Eller and A Denoth. 1996. A capacitive soil moisture sensor. Journal of Hydrology. 185, 1-4 (1996), 137-146. https://doi.org/10.1016/0022-1694(95)03003-4.
W Gardner and D Kirkham. 1952. Determination of soil moisture by neutron scattering. Social Science. 73, 5 (1952), 391-402.
H Gerhards and et. al. 2008. Continuous and simultaneous measurement of reflector depth and average soil-water content with multichannel ground-penetrating radar. Geophysics 73 (2008), Issue 4. https://doi.org/10.1190/1.2943669.
M Gotcher and et. al. 2017. Smart Irrigation Technology: Controllers and Sensors. https://extension.okstate.edu/fact-sheets/smartirrigation-technology-controllers-and-sensors.html.
G Griffiths-Sattenspiel and W Wilson. 2009. The Carbon Footprint of Water. https://www.csu.edu/cerc/researchreports/documents/CarbonFootprintofWater-RiverNetwork-2009.pdf.
J. A Huisman and et. al. 2003. Measuring soil water content with ground penetrating radar: A review. Vadose Zone Journal 2 (2003), 476-491.
F Jonard and et. al. 2012. Accounting for soil surface roughness in the inversion of ultrawideband off ground GPR signal for soil moisture retrieval. Geophysics 77 (2012). Issue 1. https://doi.org/10.1190/geo2011-0054.1.
G Kargas and et. al. 2020. The Effect of Soil Iron on the Estimation of Soil Water Content Using Dielectric Sensors. Water 12, 598 (2020).
U. M Khan, R. H Venkatnarayan, and M Shahzad. 2020. RFMap: Generating Indoor Maps using RF Signals. In IPSN. 133-144. https://doi.org/10.1109/IPSN48710.2020.00-40.
A Klotzsche and et. al. 2018. Measuring Soil Water Content with Ground Penetrating Radar: A Decade of Progress. Vadose Zone Journal (2018).
S Lambot and et. al. 2004. Modeling of Ground-Penetrating Radar for Accurate Characterization of Subsurface Electric Properties. IEEE Transactions on Geoscience and Remote Sensing 42, 11 (2004).
E Lee and S Kim. 2017. Pattern similarity based soil moisture analysis for three seasons on a steep hillslope. Journal of Hydrology 551 (2017), 484-494. https://doi.org/10.1016/j.jhydrol.2017.06.028.
B Levitas and et. al. 2011. UWB based oil quality detection. In ICUWB. IEEE, 220-224. https://doi.org/10.1109/ICUWB.2011.6058832.
L. A Richards. 1942. Soil moisture tensiometer materials and construction. Social Sci. 53, 4 (1942), 241-248.
R Selmic and et. al. 2010. Ultra-wideband signal propagation experiments in liquid media. IEEE Transactions on Instrumentation and Measurement 59, 1 (2010).
S Seybold, J. 2005. Introduction to RF Propagation. John Wiley & Sons. pp. 193-200 https://doi.org/10.1002/0471743690.
R Sui and J Baggard. 2015. Wireless Sensor Network for Monitoring Soil Moisture and Weather Conditions. Applied Engineering in Agriculture 31, 2 (2015), 193-200.
G. C Topp, J. L Davis, and A. P Annan. 1980. Electromagnetic determination of soil water content: Measurements in coaxial transmission lines. Water Resources Research 16, 3 (1980).
H Vereecken and et. al. 2007. Explaining soil moisture variability as a function of mean soil moisture: A stochastic unsaturated flow perspective. Geophysical Research Letters 34 (2007). Issue 22.
J Wang and et. al. 2020. Soil Moisture Sensing with Commodity RFID Systems. In MobiSys. Association for Computing Machinery, New York, NY, USA, 273-285. https://doi.org/10.1145/3386901.3388940.
Q Wang and et. al. 2010. A novel soil measuring wireless sensor network. In IEEE Instrumentation Measurement Technology Conference Proceedings. IEEE, 412-415. https://doi.org/10.1109/IMTC.2010.5488224.
J Xiong and K Jamieson. 2013. ArrayTrack: A Fine-Grained Indoor Location System. Usenix NSDI (2013), 1-84.
D Zhang and G Zhou. 2016. Estimation of Soil Moisture from Optical and Thermal Remote Sensing: A Review. Sensors. 16, 8 (2016). https://doi.org/10.3390/s16081308.

* cited by examiner

CONTACTLESS SOIL MOISTURE ESTIMATION USING RADIOFREQUENCY SIGNALS

CROSS-REFERENCE TO RELATED APPLICATIONS

This application claims priority to and the benefit of U.S. Provisional Patent Application No. 63/485,592, filed Feb. 17, 2023, which is incorporated herein by reference in its entirety.

BACKGROUND

With the growing realization of the need to cut carbon emissions and conserve water, the idea of smart irrigation enabled by automated soil moisture measurements has become increasingly important. The goal of these automated measurements is to estimate the amounts of water required by different parts of a field and to optimize the irrigation schedule. This smart irrigation approach is in contrast to the traditional approaches where either the watering schedule is fixed or is manually assessed by a farmer.

Automated and fine-grained soil moisture measurements have the potential to provide three crucial benefits. First, they help conserve water by enabling the farmers to adjust watering schedules based on the actual water requirements of the field. According to an estimate, up to 50% of the 9 billion gallons of water used daily for irrigation around the world is wasted due to overwatering. Such wastage can be significantly reduced through regular monitoring of soil moisture. For example, reported an average water saving of 30% in the US commercial landscapes with smart irrigation based approaches. Second, automated soil moisture measurements can reduce carbon emissions by reducing the amount of required water to irrigate a field. The carbon-dioxide that is released as a result of irrigation constitutes 5% of the total carbon emissions in the US. Third, automated soil moisture measurements can improve crop yield by ensuring that the crops are not over or under-watered.

Prior techniques to measuring soil moisture include contact-based techniques, which include inserting a probe, such as capacitive sensors, RFID tags, and metallic rods at a known depth under the surface of the soil. Such techniques have three main limitations. First, installing sensors in cultivated fields is prohibitively inconvenient because a farmer has to carefully dig a hole for each sensor and mark them to be able to locate them in future. This is made further inconvenient by the need to plough the field between successive crop cycles: sensors need to be removed before ploughing and reinstalled after ploughing. Second, contact-based techniques provide only localized measurements that reflect moisture content only at the specific locations where the sensors are installed. In many scenarios, the soil moisture is different in different locations of a field due to a number of factors such as changes in elevation and proximity to irrigation lines. In such settings, to characterize the soil moisture throughout the field, multiple sensors are required. Third, to monitor a large field, the contact-based techniques require a large number of sensors, which significantly increases the cost and complexity. Furthermore, when multiple sensors are used, an expert survey is usually required to identify representative points in a field that best characterize the overall soil conditions. As an alternative, contactless techniques have emerged in the field of soil moisture measurements.

SUMMARY

One implementation of the present disclosure is a system for contactless moisture estimation of soil, the system including: an antenna array including a first antenna configured to transmit radiofrequency (RF) signals and a plurality of second antennas configured to receive RF signals; and a controller electrically coupled to the antenna array, the controller configured to: emit, via the first antenna and into the soil, RF signals at each of a plurality of frequency increments (δf) ranging from a lower frequency (fs) to an upper frequency (fe); determine a channel frequency response (CFR) for each of the plurality of frequency increments (δf) by measuring an amplitude attenuation and a phase change of reflected RF signals detected by the plurality of second antennas; determine a power delay profile (PDP) for each of the plurality of second antennas based on the CFR of each of the plurality of frequency increments (δf); extract a subset of the reflected RF signals associated with the emitted RF signals by performing peak detection on the PDP of each of the plurality of second antennas; and for each layer of the soil and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

In some aspects, the lower frequency (fs) is 2 GHz and the upper frequency (fe) is 3 GHz.

In some aspects, the controller is further configured to filter out non-soil related reflections from the subset of the reflected RF signals by removing peaks that do not appear in the PDP of each of the plurality of second antennas.

In some aspects, the controller is further configured to verify that a phase of the peaks detected in the PDP of each of the plurality of second antennas follow a linearly increasing pattern to filter out non-soil related reflections from the subset of the reflected RF signals.

In some aspects, the plurality of frequency increments (δf) are contiguous.

In some aspects, the plurality of second antennas includes at least three equidistantly spaced antennas.

In some aspects, the estimated moisture content of each layer is estimated using a Topp equation.

In some aspects, the controller includes an RF generator to generate the RF signals.

In some aspects, the RF generator is a software defined radio (SDR).

In some aspects, the controller includes a communications interface to communicate with a remote computing device.

Another implementation of the present disclosure is a method of contactless moisture estimation of soil, the method including: emitting, via a first antenna and into the soil, radiofrequency (RF) signals at each of a plurality of frequency increments (δf) ranging from a lower frequency (fs) to an upper frequency (fe); determining a channel frequency response (CFR) for each of the plurality of frequency increments (δf) by measuring an amplitude attenuation and a phase change of reflected RF signals detected by a plurality of second antennas; determining a power delay profile (PDP) for each of the plurality of second antennas based on the CFR of each of the plurality of frequency increments (δf); extracting a subset of the reflected RF signals associated with the emitted RF signals by performing peak detection of the PDP of each of the plurality of second antennas; and for each layer of the soil and for each of the subset of reflected RF signals, determining: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

Yet another implementation of the present disclosure is a non-transitory computer readable medium having instructions stored thereon that, when executed by a computing device, cause the computing device to: operate a radiofrequency (RF) generator to emit, via a first antenna and into a medium, RF signals at each of a plurality of frequency increments (δf) ranging from a lower frequency ($f_s$) to an upper frequency ($f_e$); determine a channel frequency response (CFR) for each of the plurality of frequency increments (δf) by measuring an amplitude attenuation and a phase change of reflected RF signals detected by a plurality of second antennas; determine a power delay profile (PDP) for each of the plurality of second antennas based on the CFR of each of the plurality of frequency increments (δf); extract a subset of the reflected RF signals associated with the emitted RF signals by performing peak detection of the PDP of each of the plurality of second antennas; and for each layer of the medium and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

Figure 1:
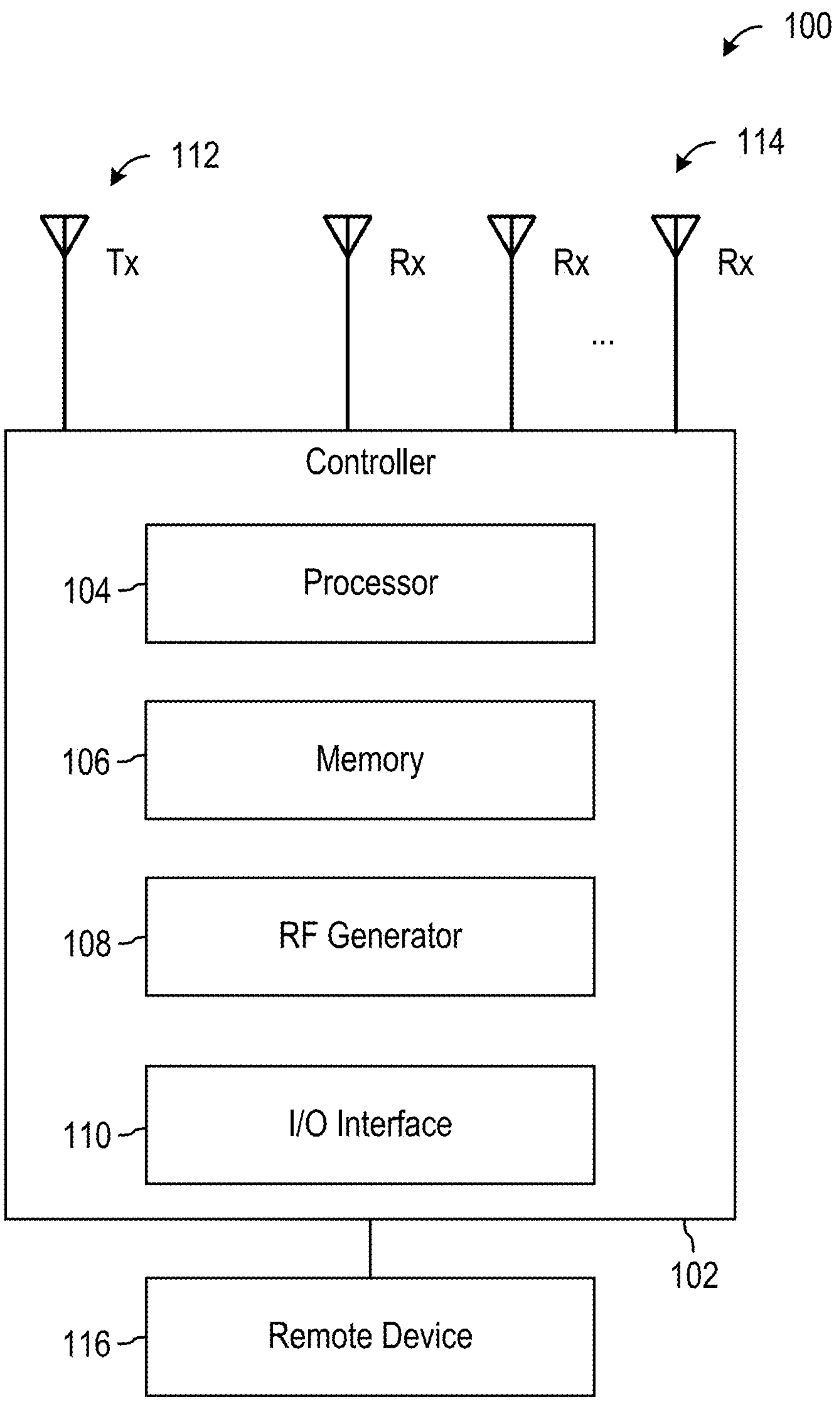
FIG. 1 is a block diagram of a contactless moisture estimation system, according to some implementations.

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Referring generally to the figures, a system, device, and methods for contactless soil moisture estimation are shown, accordingly to various implementations. Also referred to herein as CoMEt (Contactless Moisture Estimation), the disclosed system, device, and method follow a radiofrequency (RF) based approach that measures soil moisture at multiple depths underneath the ground surface without installing any objects in the soil and without making any contact with the ground surface. The main insight behind CoMEt is that the phase of an RF signal depends on its wavelength in the medium through which it is propagating, which in turn depends on the amount of soil moisture. To measure soil moisture, CoMEt leverages the phase changes across successive antennas in a receive antenna array along with the time of flight of the received signal to jointly estimate the depth of each layer of soil and the wavelength of the signal in each layer. These estimates are then used to obtain the amount of moisture in each layer of soil.

Notably, the contactless approach described herein 1) can measure soil moisture at multiple depths underneath the ground surface, 2) does not require installing any objects in the soil, 3) does not require any physical contact with the soil surface, and 4) does not require large position offsets. Such a system or device can be deployed on a drone that can fly over an entire field, collect measurements, and generate a fine-grained view of soil moisture at multiple depths for the entire field, for example.

Unlike the contact-based techniques, the contactless techniques do not install sensors in the soil. Instead, they employ RF signals to estimate soil moisture either using the time of flight (ToF) or the surface soil reflectivity. Prior contactless techniques have three important limitations. First, the ToF-based techniques require measurements at several positions to estimate soil moisture. For example, uses a measurement setup that collects data at 25 different position offsets spanning 16.5 meters. This not only makes such techniques practically unusable, but also makes assumptions that the soil moisture and composition are the same at all position offsets. Second, the surface-reflection based techniques are very sensitive to the roughness of the soil surface. Furthermore, as these techniques rely on reflections of RF signals from the surface, they can only measure the moisture content for the soil that is near the surface but not deeper under the surface. Third, prior contactless techniques cannot measure soil moisture at multiple desired depths, rather only return a single averaged estimate of moisture content near the soil surface.

Current contactless moisture estimation techniques may use RF signals to monitor soil moisture without placing any sensors in the soil. These techniques can be classified into two types: surface reflection based and ToF-based. The surface reflection based techniques indirectly measure soil moisture from soil reflectivity by modelling various soil characteristics. In one example, a surface reflection based method has been proposed to characterize subsurface electric properties from ground-penetrating radars through inverse modelling. Subsequent studies point out the limitations of this approach such as the requirement for soil and antenna specific calibrations and limited depth penetration. In another example, calibration models to take into account the roughness of soil surface in estimating soil moisture. Unfortunately, despite these calibrations, the surface reflection based techniques do not generalize well to a broad set of soil conditions and can only characterize the upper regions of soil subsurface.

ToF-based techniques leverage the principle that RF signals travel slower in soil than in air to estimate soil moisture. These techniques can be further categorized as single-offset and multi-offset. In single-offset techniques, the measurements are collected at a single position offset. As the travel time of the reflected signal depends on the reflector depth as well as the soil's dielectric permittivity, the single-offset techniques require a human operator to manually input soil depth measurements before these techniques can estimate soil moisture. In multi-offset techniques, the measurements are collected at multiple position offsets and then combined to estimate the average soil depth. One proposed multi-offset technique collects data at 25 different position offsets spanning 16.5 m to measure soil moisture. Another reduces the total span of offsets to 3 m but requires manual soil-specific calibrations to apply the soil inverse modelling technique, which depends on factors such as soil roughness. For accurate results, it further assumes that the soil moisture at nearby locations is known. These techniques also require the soil composition to stay uniform throughout all position offsets. Furthermore, no prior technique measures the soil moisture at multiple depths, rather they measure the average amount of moisture up to a certain depth.

Researchers have proposed a wide range of contact-based sensors for measuring soil moisture. Some examples include electrical resistance based sensors, capacitive sensors, heat diffusion sensors, tensiometers, and radioactive sensors. All of these sensors estimate soil moisture by measuring an appropriate soil property that is sensitive to moisture. These sensors require careful installation and are connected to a central hub that fetches data from these sensors either through wired or through wireless connections. In addition, there are some RF-based approaches as well that install some object under the soil to estimate soil moisture. In one example, metallic rods are placed in soil to enhance the reflections of RF signal from soil and to determine the depth of those reflections. Similarly, another example places RFID tags in soil at known depths to measure soil moisture. Unfortunately, all these techniques suffer from the three limitations that we described above, e.g., difficult installation, localized measurements, and high deployment cost due to the infeasibility of mounting these sensors on a mobile platform.

Other techniques may rely on ToF of RF signals through the material. For example, a material under study is placed between the transmit and receive antennas and precisely know the distance traversed by the RF signal. This, however, is not possible when measuring soil moisture as the transmit and receive antennas both have to be on the same side of (i.e., above) the soil and the RF signals reflect back from multiple unknown depths. This renders such prior work unusable for estimating soil moisture.

CoMEt System

Referring now to FIG. 1, a block diagram of CoMEt—more generally, a contactless moisture estimation system 100—is shown, according to some implementations. System 100 generally consists of an antenna array that includes at least one transmit antenna 112 and a plurality of receive antennas 114 arranged as an equally spaced receive (Rx) antenna array. It should be appreciated that system 100 may generally include any number of receive antennas (e.g., R antennas). In some implementations, the antennas in the antenna array are placed side-by-side with a spacing of Δtr between the transmit antenna 112 and the first receive antenna 114 of the Rx antenna array, and Δr between successive receive antennas 114 in the array. System 100 also includes a controller 102 which is electrically coupled to the transmit antenna 112 and the receive antennas 114.

Controller 102 is shown to include a processor 104 and a memory 410. Processor 104 can be a general-purpose processor, an application specific integrated circuit (ASIC), one or more field programmable gate arrays (FPGAs), a group of processing components, or other suitable electronic processing structures. In some embodiments, processor 104 is configured to execute program code stored on memory 106 to cause controller 102 to perform one or more operations, as described below in greater detail. It will be appreciated that, in embodiments where controller 102 is part of another computing device, such as a general-purpose computer, the components of controller 102 may be shared with, or the same as, the host device.

Memory 106 can include one or more devices (e.g., memory units, memory devices, storage devices, etc.) for storing data and/or computer code for completing and/or facilitating the various processes described in the present disclosure. In some embodiments, memory 106 includes tangible (e.g., non-transitory), computer-readable media that stores code or instructions executable by processor 104. Tangible, computer-readable media refers to any physical media that is capable of providing data that causes controller 102 to operate in a particular fashion. Example tangible, computer-readable media may include, but is not limited to, volatile media, non-volatile media, removable media and non-removable media implemented in any method or technology for storage of information such as computer readable instructions, data structures, program modules or other data. Accordingly, memory 106 can include RAM, ROM, hard drive storage, temporary storage, non-volatile memory, flash memory, optical memory, or any other suitable memory for storing software objects and/or computer instructions. Memory 106 can include database components, object code components, script components, or any other type of information structure for supporting the various activities and information structures described in the present disclosure. Memory 106 can be communicably connected to processor 104 and can include computer code for executing (e.g., by processor 104) one or more processes described herein.

While shown as individual components, it will be appreciated that processor 104 and/or memory 106 can be implemented using a variety of different types and quantities of processors and memory. For example, processor 104 may represent a single processing device or multiple processing devices. Similarly, memory 106 may represent a single memory device or multiple memory devices. Additionally, in some embodiments, controller 102 may be implemented within a single computing device (e.g., one server, one housing, etc.). In other embodiments, controller 102 may be distributed across multiple servers or computers (e.g., that can exist in distributed locations). For example, controller 102 may include multiple distributed computing devices (e.g., multiple processors and/or memory devices) in communication with each other that collaborate to perform operations. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers.

Controller 102 is further shown to include a radiofrequency (RF) generator 108 that can generate RF signals for transmission via transmit antenna 112. Specifically, RF generator 108 can be configured to generate RF signals across a range of frequencies which can, at the direction of processor 104, be emitted by transmit antenna 112. In some implementations, RF generator 108 is a software defined radio (SDR). Controller 102 is also shown to include an input/output (I/O) interface 110 that facilitates communications between controller 102 and any external components or devices, including a remote device 116, which may be a general purpose computer, a smartphone, a tablet, or any other computing device. For example, I/O interface 110 can provide means for transmitting data to, or receiving data from, remote device 116. Accordingly, I/O interface 110 can be or can include a wired or wireless communications interface (e.g., jacks, antennas, transmitters, receivers, transceivers, wire terminals, etc.) for conducting data communications, or a combination of wired and wireless communication interfaces. In some embodiments, communications via I/O interface 110 are direct (e.g., local wired or wireless communications) or via a network (e.g., a WAN, the Internet, a cellular network, etc.). For example, I/O interface 110 may include one or more Ethernet ports for communicably coupling controller 102 to a network (e.g., the Internet). In another example, I/O interface 110 can include a WiFi, Bluetooth®, or other short-range wireless transceiver for communicating via a wireless communications network. In yet another example, I/O interface 110 may include cellular or mobile phone communications transceivers.

In some implementations, I/O interface 110 is configured to receive or detect reflected RF signals obtained by receive antennas 114. "Reflected" RF signals are signals that are reflected back from a medium that is being measured (e.g., soil) for moisture estimation. Accordingly, I/O interface 110 may include an RF receiver or transceiver. In some implementations, RF generator 108 may be integrated into I/O interface 110 and/or certain functionality of I/O interface 110 may be performed by RF generator 108, based on the particular configuration of controller 102. In any case, when in use, the antenna array of system 100 (e.g., antennas 112, 114) are placed at a height of $d_0$ above the soil surface. To measure soil moisture, system 100 first sweeps a frequency spectrum from $f_s$ to $f_e$ in increments of $\delta_f$. At each frequency increment and at each receive antenna, the system 100—or, more specifically, controller 102—estimates the channel frequency response (CFR) by measuring the amplitude attenuation and phase change in the received signal. Next, a power delay profile (PDP) is calculated using these CFR values. As there are R receive antennas, system 100 generally obtains R PDPs. The peaks in the PDP show the time-of-flights (ToFs) of various reflections from the soil surface as well as the soil layers underneath.

As described herein, a soil "layer" is generally defined as a layer parallel to the soil surface whose permittivity distinctly differs from the layers above and beneath. There is often no well-defined boundary between layers because the moisture content changes as a gradient as we go deeper underneath the surface. Nonetheless, for any two stacked sections or "chunks" of soil with certain heights, as long as the average moisture content in the upper chunk is different from that in the chunk below it, each section can be generally considered as a distinct layer. As changes in permittivity cause reflections in the transmit signal, system 100 receives distinct reflections from the soil layers with different moisture contents. While generally described herein with respect to soil, it should also be appreciated that system 100 may be configured to estimate moisture in other mediums.

After estimating the PDP, for each RF reflection observed in the PDP, controller 102 determines if it is arriving back from a layer of soil or from another object in the vicinity. For each reflection from a layer of soil, controller 102 leverages the phase changes across successive antennas in the Rx antenna array to jointly estimate the depth of that layer and the wavelength of the signal in that layer. Next, controller 102 calculates the dielectric permittivity for each layer using the estimated wavelength of the signal in that layer. Finally, it obtains the amount of moisture content in each layer using the Topp Equation, which translates the values of dielectric permittivity into the amount of moisture in soil.

There were, of course, a number of challenges faced when designing system 100, which are generally addressed by the implementation of system 100 described herein. The first challenge is that the depth of each soil layer from which the RF signals reflect back is not known. To address this challenge, system 100 leverages both ToF and phase changes across antennas in the antenna array and combines them to jointly estimate the soil moisture and soil depth. It was found that the phase change across two antennas depends both on the signal wavelength and soil depth. Therefore, with the two independent observations of ToF and phase change, system 100 can resolve the two unknown parameters, e.g., signal wavelength and soil depth. Furthermore, as the phase changes considerably across antennas in the antenna array even when they are spaced a few centimeters apart, the approach described herein does not require placing antennas at large position offsets.

The second challenge is that reflections could be received from multiple layers of soil with distinct amounts of soil moisture. Unfortunately, the process of measuring soil moisture for the upper-most layer does not directly generalize to the lower layers because the soil moisture estimates of the upper layers affect the estimates of the lower layers. To address this challenge, controller 102 derives a general estimate by relating the lengths of reflections from each layer to the overall reflection length, and then uses an iterative approach to measure the soil moisture at each layer. Moreover, as the antennas of system 100 do not touch the soil surface (rather are at a certain height above it) the medium between the setup and the soil surface (i.e., air) acts as another layer that affects the soil moisture estimates of the subsequent layers. This is addressed by treating air as the first layer in the multi-depth soil moisture estimation.

The third challenge is that the Rx antenna array, receive antennas 114, may receive reflections from non-soil objects in the environment in addition to the reflections from soil layers. These non-soil reflections are particularly challenging in indoor environments, such as greenhouses, where there may be several indoor reflectors. Highly directional antennas are large in size, rendering them unusable for creating an antenna array, and thus are not a suitable solution to this issue. Instead, directional antennas with larger beamwidths are utilized. Notably, for the reflections from soil, the phase shifts at successive antennas in the Rx antenna array (receive antennas 114) increase noticeably, whereas they do not follow this pattern for the non-soil reflections. This is because compared to the non-soil reflections, soil reflections form relatively smaller angles of arrival (AoA). System 100 leverages this observation to separate soil reflections from non-soil reflections by checking that each reflection follows the pattern of increasing phase changes across successive antennas.

Figure 2:
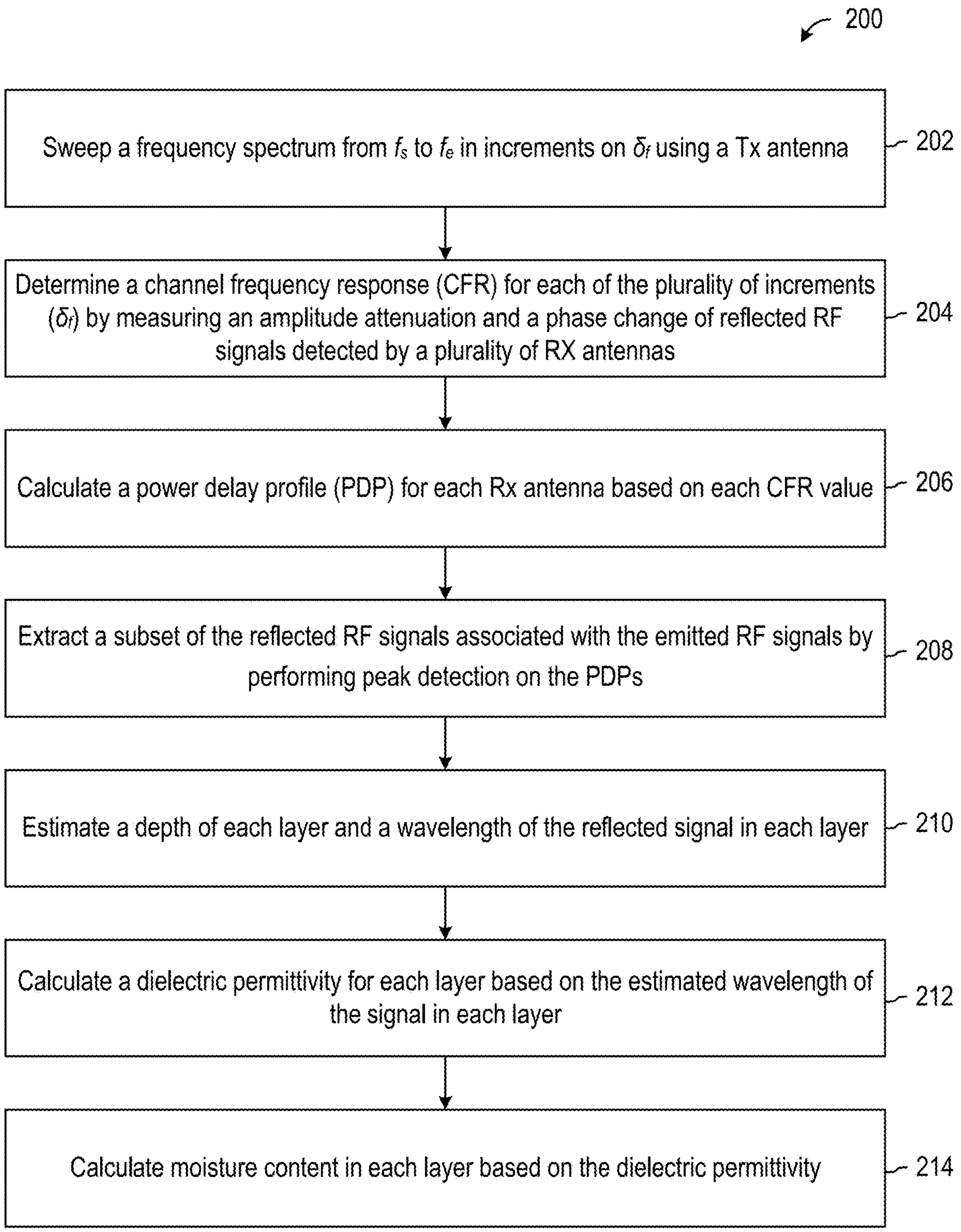
FIG. 2 is a flow chart of a process for estimating soil moisture using radiofrequency (RF) signals, according to some implementations.

Referring now to FIG. 2, a flow chart of a process 200 for estimating soil moisture using radiofrequency (RF) signals is shown, according to some implementations. In some implementations, process 200 is implemented by system 100, as described above. Specifically, in some implementations, process 200 is implemented by controller 102. It will be appreciated that certain steps of process 200 may be optional and, in some implementations, process 200 may be implemented using less than all of the steps. It will also be appreciated that the order of steps shown in FIG. 2 is not intended to be limiting.

At step 202, a frequency spectrum ranging from $f_s$ to $f_e$ is swept in increments of $\delta_f$. Put another way, controller 102 may, individually or by controlling RF generator 108, emit, via transmit antenna 112, RF signals and into the soil at each of a plurality of frequency increments ($\delta_f$) ranging from a lower frequency ($f_s$) to an upper frequency ($f_e$). In some implementations, lower frequency ($f_s$) is 2 GHz and the upper frequency ($f_e$) is 3 GHZ; although, it should be appreciated that the present disclosure is not limited to only this frequency range. Generally, the frequency increments ($\delta_t$) are contiguous or sequential.

At step 204, a channel frequency response (CFR) for each of the plurality of increments ($\delta_f$) is determined by measuring an amplitude attenuation and a phase change of reflected RF signals detected by receive antennas 114. From the CRFs, at step 206, a power delay profile (PDP) for each of the receive antennas 114 is determined. At step 208, a subset of the reflected RF signals associated with the emitted RF signals (e.g., from step 202) are extracted by performing peak detection on the PDPs. In some implementations, during or after step 208, controller 102 may also ensure that the phases of the peaks across receive antennas 114 follow a linearly increasing pattern by evaluating the PDPs. Then, for each layer of the soil and for each of the subset of reflected RF signals, determine: i) a wavelength of the reflected RF signal in the layer, ii) an estimated depth of the layer, iii) a dielectric permittivity of the layer based on the wavelength in the layer, and iv) an estimated moisture content of the layer based on the dielectric permittivity. Specifically, at step 210, a depth of each layer of the soil is estimated, as well as a wavelength of the signal in the layer. At step 212, a dielectric permittivity is calculated for each layer of the soil based on the estimated wavelength of the signal in that layer. Finally, at step 214, the moisture content in each layer is calculated from the dielectric permittivity. In some implementations, moisture content is calculated using the Topp equation.

Figure 3:
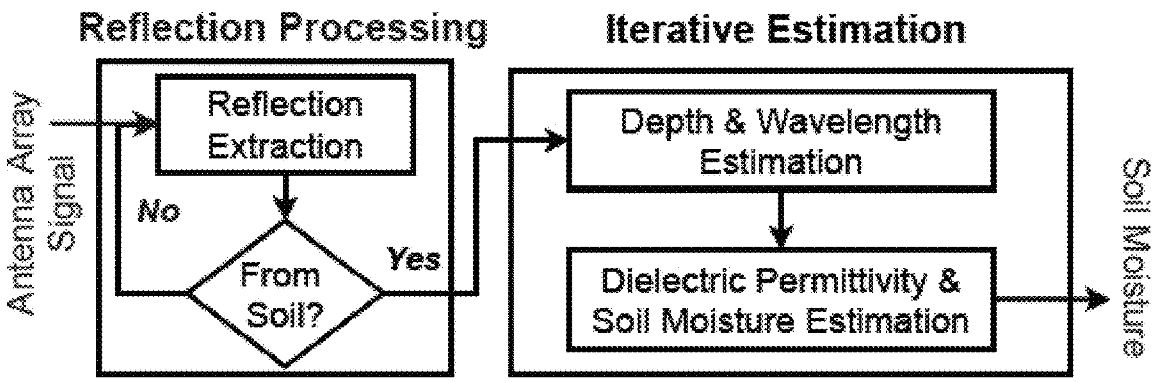
FIG. 3 is a block diagram that illustrates the processing of a received RF signal, according to some implementations.

Certain steps of process 200 are also illustrated more generally in the block diagram of FIG. 3, which is a high-level block diagram of CoMEt, according to some implementations. As shown in FIG. 3, the goal of the reflection processing module is to decompose the received signal into its constituent reflections that arrive from different soil layers and filter out any reflections that do not originate from a soil layer. This module consists of two blocks-a reflection extraction block and an iterative estimation block. Recall that a layer refers to a chunk of (sub-surface) soil with a distinct amount of soil moisture that reflects back the transmitted RF signal. To extract reflections from each layer, this block first estimates the CFR in the frequency domain for each frequency from $f_s$ to $f_e$ in increments of $\delta_f$, and then maps them to time domain by taking IFFT of all $\lfloor(f_e-f_s)/\delta_f\rfloor+1$ CFR values. This results in the PDP, which characterizes the channel as a function of time. The reflections from different layers of the soil show up as peaks in PDP. This module applies a peak detection algorithm on PDP and outputs as many reflections as the number of layers of soil visible to CoMEt. Each reflection is expressed as a complex number constituting an amplitude and a phase. If the received signal contains reflections from some non-soil reflectors, then it outputs those reflections as well. The resolution of PDP is determined by the bandwidth $f_s-f_e$ of the frequency sweep and is given by $f_s-f_e \times c/2$, where c is the speed of the signal in free space.

The non-soil reflection filtering block determines whether any given reflection extracted by the reflection extraction block above was returned from a layer of soil or from some other object in the vicinity and discards any reflections that were not generated by a layer of soil. To perform this filtering, this block leverages the observation that the phase shifts at successive antennas in the Rx antenna array (receive antennas 114) increase significantly for the reflections from soil but not so much for the non-soil reflection. It was also observed, during experimentation, that some reflections appear in PDPs that actually do not represent valid reflections. These reflections occur because as the RF signals attenuate significantly under soil, different antennas can receive different dominant reflections, resulting in ambiguous peaks. Similarly, a peak in PDP may simply be due to noise. Accordingly, the non-soil reflection filtering block can be configured to discard all such invalid reflections. Notably, while the phase shifts at the successive antennas increase for valid soil reflections, they do not follow any such pattern for the invalid reflections, as demonstrated in FIG. 5.

The goal of the iterative estimation module is to estimate the amount of moisture in each soil layer using the signal reflected by that layer. This module starts by estimating the moisture content of the soil layer at the top and then iteratively proceeds to estimate the moisture in each lower layer. Unlike prior approaches, the present disclosure does not assume that either the depth of soil or the depth of any layer of soil is known. Accordingly, the depth and wavelength estimation block takes all the reflections from the "Non-Soil Reflection Filtering" block and uses this system of equations to jointly estimate the depth of each soil layer as well as the wavelength of the signal in that layer.

Next, the Dielectric Permittivity and Soil Moisture Estimation block first uses a well-known result about the relationship of dielectric permittivity of a material with the wavelength of the signal travelling through that material. Leveraging this relationship, it plugs the values of the wavelengths estimated by the previous block to estimate the permittivity of each soil layer. Next, it uses another well-known result, known as Topp Equation, which expresses the moisture content in a soil sample as a function of the dielectric permittivity of that soil sample. Leveraging this result, this block plugs in the dielectric permittivity just estimated for each layer into the Topp Equation to estimate the amount of moisture in each soil layer.

Examples

Described in herein, is an example contactless approach 1) to measure soil moisture at multiple depths underneath the ground surface, 2) does not require installing any objects in the soil, 3) does not require any physical contact with the soil surface, and 4) does not require large position offsets. It is contemplated that the described system may be deployed on a drone that can fly over an entire field, collect measurements, and generate a fine-grained view of soil moisture at multiple depths for the entire field. Provided herein are the theoretical foundation for such a contactless soil moisture measurement system, its design, implementation, and evaluation.

Figure 6:
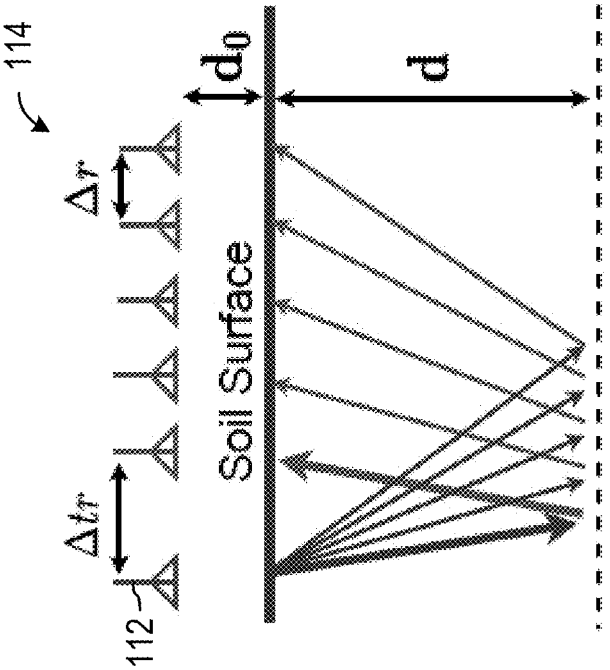
FIG. 6 is a diagram of an example configuration of the contactless moisture estimation system antenna array, according to some implementations.

A Contactless Moisture Estimation (hereafter CoMEt) approach is presented that used RF signals to measure soil moisture while satisfying the four requirements listed above. CoMEt included a transmit antenna and R receive antennas arranged as an equally spaced receive (Rx) antenna array. The antennas were placed side-by-side with a spacing of Δtr between the transmit antenna and the first element of the Rx antenna array, and Δr between successive antennas in the array, as shown in FIG. 6.

Contactless Moisture Estimation: Two types of contactless techniques have been used in the state of the art, surface reflection based and ToF-based, which use RF signals to monitor soil moisture.

The surface reflection based techniques indirectly measure soil moisture from soil reflectivity by modelling various soil characteristics [28, 31, 32]. In a known method [32], subsurface electric properties are characterized from ground-penetrating radars through inverse modelling. Subsequent studies point out the limitations of this approach such as the requirement for soil and antenna specific calibrations and limited depth penetration [28, 31]. In another known method [28], calibration models are used which take account of the roughness of soil surface in estimating soil moisture. Unfortunately, despite these calibrations, the surface reflection based techniques do not generalize well to a broad set of soil conditions, and can only characterize the upper regions of soil subsurface [31]. The ToF-based techniques leverage the principle that RF signals travel slower in soil than in air to estimate soil moisture [16, 24, 27]. These techniques can be further categorized as single-offset and multi-offset. In single-offset techniques, the measurements are collected at a single position offset [27]. As the travel time of the reflected signal depends on the reflector depth as well as the soil's dielectric permittivity, the single-offset techniques require a human operator to manually input soil depth measurements before these techniques can estimate soil moisture. In multi-offset techniques, the measurements are collected at multiple position offsets and then combined to estimate the average soil depth [16, 24]. A multi-offset technique collects data at twenty-five different position offsets spanning 16.5 m to measure soil moisture. Another known technique [24], reduces the total span of offsets is reduced to 3 m but requires manual soil-specific calibrations to apply the soil inverse modelling technique, which depends on factors such as soil roughness and additionally assumes that the soil moisture at nearby locations is known. The ToF techniques also require the soil composition to stay uniform throughout all position offsets. Furthermore, the known techniques do not take soil moisture measurements at multiple depths, rather they measure the average amount of moisture up to a certain depth.

Contact-based Moisture Estimation: A wide range of contact-based sensors for measuring soil moisture have been known in the art. Some examples include electrical resistance based sensors [17], capacitive sensors [22], heat diffusion sensors [44], tensiometers [35], and radioactive sensors [23]. All of these sensors estimate soil moisture by measuring an appropriate soil property that is sensitive to moisture. These sensors require careful installation and are connected to a central hub that fetches data from these sensors either through wired [3, 4] or through wireless connections [38, 42]. In addition, there are some RF-based approaches as well that install some object under the soil to estimate soil moisture. In one known technique [20], a few metallic rods in soil to enhance the reflections of RF signal from soil and to determine the depth of those reflections. Yet another known technique [41], places RFID tags in soil at known depths to measure soil moisture. Unfortunately, all these techniques suffer from the three limitations, difficult installation, localized measurements, and high deployment cost due to the infeasibility of mounting these sensors on a mobile platform.

Yet other known techniques use several RF-based contactless approaches to estimate various properties of different materials such as oil adulteration [34], salt concentration [36], liquid type [19], etc. These techniques rely on ToF of RF signals through the material. They place the material under study between the transmit and receive antennas and precisely know the distance traversed by the RF signal. This, however, is not possible when measuring soil moisture as the transmit and receive antennas both have to be on the same side of (i.e., above) the soil and the RF signals reflect back from multiple unknown depths. This renders such prior work unusable for estimating soil moisture.

Technical Overview

Described herein is the CoMEt system and method to measure soil moisture at multiple depths of soil without installing any sensors in the soil. FIG. 3 shows the different modules of CoMEt, and how they interact with each other.

Reflection Processing. The reflection processing module decomposed the received signal into its constituent reflections that arrive from different soil layers and filter out any reflections that do not originate from a soil layer. The reflection processing module consists of two blocks, reflection extraction and non-soil reflection filtering.

Reflection Extraction. Recall that a layer refers to a chunk of (sub-surface) soil with a distinct amount of soil moisture that reflects back the transmitted RF signal. To extract reflections from each layer, this block first estimates the CFR in the frequency domain for each frequency from $f_s$ to $f_e$ in the increments of δf, and then maps them to time domain by taking IFFT of all $\lfloor (f_e - f_s)/\delta_f \rfloor + 1$ CFR values. This results in the PDP, which characterizes the channel as a function of time. The reflections from different layers of the soil show up as peaks in PDP. This module applies a peak detection algorithm on PDP and outputs as many reflections as the number of layers of soil visible to CoMEt. Each reflection is expressed as a complex number constituting an amplitude and a phase. If the received signal contains reflections from some non-soil reflectors, then it outputs those reflections as well. The resolution of PDP is determined by the bandwidth $f_e - f_s$ of the frequency sweep and is given by $(f_e\ f_s) \times c/2$, where c is the speed of the signal in free space [15].

Non-Soil Reflection Filtering. This block determines whether any given reflection extracted by the reflection extraction block above was returned from a layer of soil or from some other object in the vicinity and discards any reflections that were not generated by a layer of soil. To perform this filtering, this block leverages our observation that the phase shifts at successive antennas in the Rx antenna array increase significantly for the reflections from soil but not so much for the non-soil reflections.

Iterative Estimation. The iterative estimation module estimates the amount of moisture in each soil layer using the signal reflected by that layer. This module starts by estimating the moisture content of the soil layer at the top and then iteratively proceeds to estimate the moisture in each lower layer. The iterative estimation module includes two blocks.

Depth and Wavelength Estimation. Unlike the known techniques, the system and method of CoMEt does not make the assumption that either the depth of soil or the depth of any layer of soil is known. To avoid this assumption, a system of equations is used that relies on the knowledge of the distance between transmit and receive antennas, the phase changes observed in the signal received at successive antennas of the Rx antenna array, and the ToFs of various reflections. This block takes all the reflections from the Non-Soil Reflection Filtering block and uses this system of equations to jointly estimate the depth of each soil layer as well as the wavelength of the signal in that layer.

Dielectric Permittivity and Soil Moisture Estimation. This block first uses a well-known result from prior literature about the relationship of dielectric permittivity of a material with the wavelength of the signal travelling through that material. Leveraging this relationship, the values of the wavelengths estimated by the previous block are used to estimate the permittivity of each soil layer. Next, the calculated dielectric permittivity is applied to another well-known result from literature, known as The Topp Equation [39], which expresses the moisture content in a soil sample as a function of the dielectric permittivity of that soil sample, is used to estimate the amount of moisture in each soil layer.

Reflection Processing

In any environment, the received signal is a sum of multiple reflections. First, the constituent reflections were extracted from the received signal. Then, the moisture content of the soil layers was estimated. In the disclosed system and method, CoMEt was used to distinguish between the reflections from soil and from other objects in the environment.

Reflection Extraction. A straightforward way to extract reflections is to transmit a short pulse and measuring the time instants when each reflection of that pulse arrives back. However, since the RF reflections arrived at sub nanosecond intervals, sampling these reflections required expensive and precise hardware. Instead, CoMEt used PDPs to extract the reflections.

Estimating the PDP. To obtain PDP, a signal was repeatedly transmitted at contiguous frequencies. After the transmission at any given frequency, the channel frequency response was estimated at that frequency using the signal received at each receive antenna. Each channel frequency response was represented by a complex number, where the magnitude of the complex number denoted the attenuation caused by the channel at that frequency and the phase of the complex number denoted the phase shift caused by the channel. If a signal transmitted at frequency f has unit amplitude and zero phase, then the channel frequency response h(f) equals the received signal, and is given by $$h(f) = \alpha e^{-j2\pi f\phi} \tag{1}$$

where α and ϕ denote the amplitude attenuation and phase offset in the received signal caused by the channel. To obtain the power delay profile, first, performing a sweep of a given frequency bandwidth from $f_s$ to $f_e$ in steps of δf and estimating the parameters α and ψ at each transmitted frequency. Next, the IFFT was computed over the sequence $\langle h(f_s), h(f_s+\delta f), h(f_s+2\delta f), \ldots, h(f_e) \rangle$ and the time domain representation of the channel was obtained, i.e., the PDP. Thereby R antennas in the Rx antenna array resulted in R PDPs.

Extracting the Reflections. The various reflections arriving at that receive antenna were isolated using PDP for any given receive antenna. Let h(t) represent the PDP, where t represents the ToF and h(t=τ) quantifies the amplitude and phase of the signal arriving at the receiver τ seconds after the signal was transmitted. Suppose there are N reflections arriving at a receive antenna at $\tau_1$ to $\tau_N$ seconds after the signal was transmitted. Then, the amplitude of PDP will contain a peak at each $t=\tau_i$, where $i \in \{1,N\}$. The amplitude and phase of the $i^{th}$ reflection is given by the complex number $h(t=\tau_i)$.

To extract the reflections arriving at the Rx antenna array and the times at which these reflections arrive, first the power of each PDP, h(t), is calculated as $\|h(t)\|^2$ and then the peak detection algorithm is used to find all the peaks in h(t). The number of peaks returned by the peak detection algorithm denotes the number of reflections, N, and the locations of these peaks denote the ToFs of the reflections. These steps are applied on the PDP obtained from each antenna in the Rx antenna array. Finally, any extraneous peaks introduced by noise are removed by keeping only those peaks that appear in the PDP of each receive antenna. For example, if the ToF of a reflection observed in the PDP of an antenna is 10 ns, then that reflection is retained only if a corresponding peak is found at 10 ns in the PDP of each of the remaining antennas as well.

Figure 4:
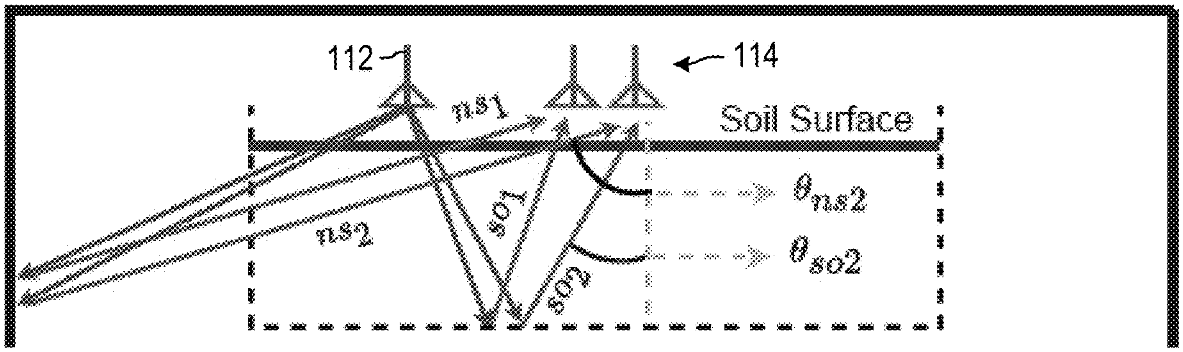
FIG. 4 is a diagram illustrating example reflections arriving at the receiving (Rx) antenna array of the contactless moisture estimation system, according to some implementations.

Non-Soil Reflection Filtering. An ideal setup should have highly directional antennas to ensure that they only receive reflections from the layers of soil and not from the objects in the vicinity. FIG. 4 shows examples of various reflections arriving at the Rx antenna array. Among these reflections, $so_1$ and $so_2$ are examples of desirable reflections coming from soil while $ns_1$ and $ns_2$ are examples of undesirable reflections coming from some non-soil objects. Unfortunately, the antenna directionality comes at the cost of antenna size, i.e., highly directional antennas are significantly larger in size. Their larger sizes render them too big to create an antenna array, wherein the antennas are closely spaced in the array, and further make them too bulky to be carried by a mobile platform, such as a drone. Thus, in the disclosed system and method, directional antennas with larger beamwidths and smaller sizes are used.

The lack of highly directional antennas results in the Rx antenna array to also receive reflections from objects other than soil, as shown by $ns_1$ and $ns_2$ in FIG. 4. This is particularly challenging indoors, such as in greenhouses, where there are many reflectors. Thus, the disclosed system and method determines whether any given reflection obtained from the PDPs is a soil reflection or a non-soil reflection, and then only the soil reflections are kept.

To distinguish between the soil and non-soil reflections, several features are used. In one instance, the antennas that are placed over the soil surface receive the non-soil reflections, which form relatively larger AoAs compared to the soil reflections. For example, in FIG. 4, $\theta_{so2} << \theta_{ns2}$. Thus, non-soil reflections may be filtered by blocking any reflections that have relatively larger AoAs. However, because the phase difference between antennas in the Rx antenna array does not only depend on the AoA of the signal but also on the medium through which the signal travels [43], it is contemplated that the identity of the medium(s) through which the signal travels must be known to accurately measure the AoAs arriving at the Rx antenna array.

The second feature relates to the change in phase across successive antennas, which is relatively much smaller for non-soil reflections than for the reflections from soil because non-soil reflections make significantly larger AoAs with receive antennas, as shown in FIG. 4. The phase shift across successive antennas is governed by sin(·) of AoA. Let $\theta_{nsi}$ represent the angle that an incoming non-soil reflection makes with the $i^{th}$ antenna in the Rx array. Similarly, let $\theta_{soi}$ represent the angle that an incoming reflection from soil makes with the $i^{th}$ antenna. As $\theta_{nsi} >> \theta_{soi}$, thus, $|\sin(nsi+1) - \sin(ns_i)| << |\sin(so_{i+1} - \sin(s_{oi})|$, i.e., the change in phase across successive antennas is much smaller for non-soil reflections compared to the reflections from the soil.

A third feature relates to the fact that the change in the phase of a given reflection at successive receive antennas depends on the dielectric permittivity of the medium through which the signal travels. In particular, the higher the dielectric permittivity of the medium, the larger the variation in phase at successive receive antennas [43]. Similar to the second insight, this means that for the soil reflections, which travel through mediums with high dielectric permittivity (i.e., the soil), the phase shift at the successive antennas would be larger. On the other hand, the phase shift at the successive antennas would be comparatively small for the non-soil reflections, which travel through air that has a much smaller dielectric permittivity compared to soil.

Figure 5:
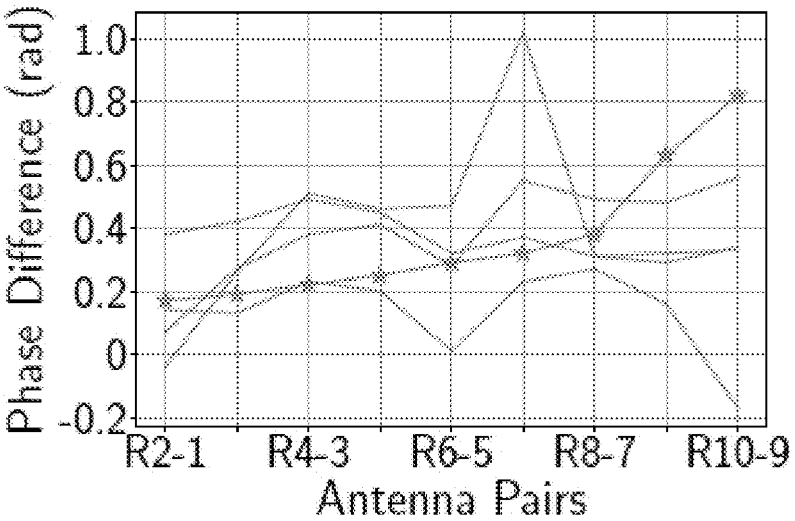
FIG. 5 is an example graph illustrating phase differences across antenna pairs, according to some implementations.

In some instances, a subset of reflections appears in PDPs that actually do not represent valid reflections. These reflections occur because as the RF signals attenuate significantly under soil, different antennas can receive different dominant reflections, resulting in ambiguous peaks. Similarly, a peak in PDP may simply be due to noise. A fourth feature relates to discarding all such invalid reflections because the phase shifts at the successive antennas increase for valid soil reflections, they do not follow any such pattern for the invalid reflections. To demonstrate this, FIG. 5 plots the phase differences observed across antenna pairs for the first five peaks in PDPs from an experiment. It is seen in FIG. 5 that the soil reflection plot, shown with orange color, follows a pattern of increasing phase changes, whereas all other plots follow random patterns.

Combining the second, third, and fourth features, for any given reflection, it was checked whether the phase of that reflection is changing considerably across successive antennas and whether this phase change is increasing across successive pairs of antennas. Let Afi denote pairs for the first five PDP peaks the difference between phases of a reflection received at two successive antennas i and i+1. For a valid reflection from a layer of soil layer of soil, the following condition must hold.

$$\Delta\xi_i < \Delta\xi_{i+1} + \gamma, \forall 1 \le i < R-1 \tag{2}$$

where R is the number of antennas in the Rx antenna array and $\gamma$ denotes an error margin. If this condition holds, that reflection is accepted as a valid reflection from a layer of soil. Otherwise, it discards it as a non-soil reflection. Finally, it is noted that some non-soil reflections may arrive from the opposite side of the antenna array. In that case, the phase shifts may decrease across successive antennas. Such reflections are also discarded.

Depth & Wavelength Estimation

Methods to jointly estimate the depth of each soil layer as well as the wavelength that the signal has when traveling through that layer are disclosed herein. First, the equations for the joint estimation were derived, assuming that there is only a single layer of soil and that the transmit and receive antennas were touching the surface of that layer. Next, the equations for joint estimation were extended to handle multiple soil layers. Finally, the realistic settings were incorporated where the transmit and receive antennas were not touching the surface, but rather were at some height above the surface.

Estimation For Single Layer. Referring now to FIG. 6, a single transmit antenna and R receive antennas were placed above the soil surface. In an example, $\Delta r$ denoted the equi-distant spacing between all the receive antennas and $\Delta tr$ denoted the spacing between the transmit antenna and the first antenna in the Rx antenna array. The length of the path traversed by the signal that reflects from under the soil was represented by $l_i$ and arrived at the $i^{th}$ antenna in the Rx antenna array, where $1 \le i \le R$. For example, in FIG. 6, $l_1$ equals the sum of the lengths of the two bold rays.

Figure 7:
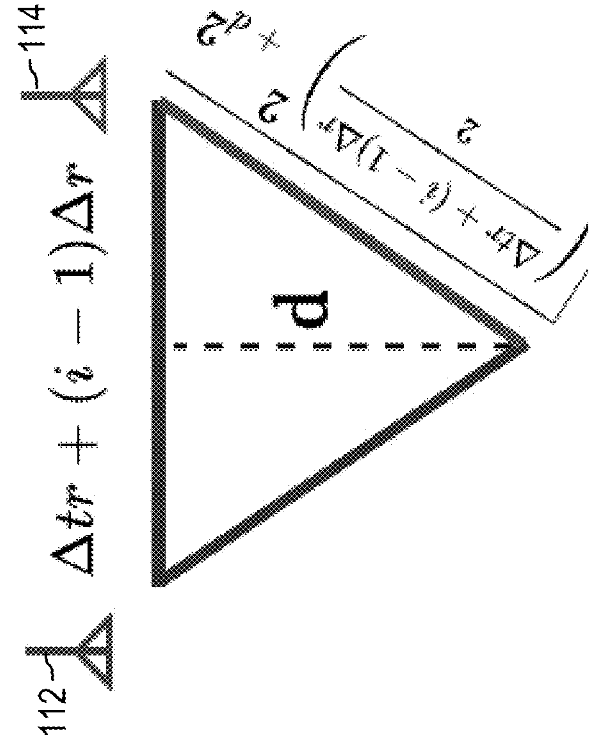
FIG. 7 is a diagram illustrating example reflection geometry of the transmitting (Tx) and Rx antennas of the contactless moisture estimation system antenna array, according to some implementations.

In one example, there was only one layer of soil whose depth is d and the receive antennas received reflections only from that layer, as shown in FIG. 6, and the transmit and receive antennas are placed on the soil surface touching it. By solving the geometry in FIG. 7, $l_i$ was expressed as follows:

$$l_i = 2\sqrt{K_i^2 + d^2}, \forall 1 \le i < R \tag{3}$$

where $K_i = 2(\Delta tr + (i-1)\Delta r)$. The difference in lengths between the soil reflections received at two successive antennas i and i+1 was denoted as $\Delta l_i$, then $\Delta l_i$ was expressed as:

$$\Delta l_i = l_{i+1} - l_i = 2\left(\sqrt{K_{i+1}^2 + d^2} - \sqrt{K_i^2 + d^2}\right) \tag{4}$$

The difference in phases of the soil reflection received at adjacent antennas i and i+1 was denoted as $\Delta\phi_i$. An increased in path length by $\Delta l_i$ changes the phase $\Delta\phi_i$ by $2\pi\Delta l_i/\lambda$ [43], where $\lambda$ was the wavelength of the signal in soil. By plugging in $\Delta l_i$ from Eq. (4), $\Delta\phi_i$ was expressed as:

$$\Delta\phi_i = \frac{4\pi}{\lambda}\left(\sqrt{K_{i+1}^2 + d^2} - \sqrt{K_i^2 + d^2}\right) \tag{5}$$

Note that the value of $\Delta\phi_i$ was known by comparing the phases of the corresponding reflections in the PDPs of antennas i and i+1. Thus, in Eq. (5), there were two unknowns: the depth of soil d and the wavelength of signal $\lambda$ when it travels through this soil. To estimate these two unknowns, another independent equation was used to relate them. It was shown that $\lambda = v_{soil}/f = li/(f \times t_i)$, where f was the center frequency of the transmit signal and $t_i$ was the ToF of the signal received at the $i^{th}$ antenna in the Rx antenna array. It was shown earlier that the value of $t_i$ can be derived from the PDP. By using the value of $l_i$ from Eq. (3), λ was expressed as:

$$\lambda = \frac{2}{ft_i}\sqrt{K_i^2 + d^2} \tag{6}$$

Substituting this value of λ into Eq. (5), as equation with only one unknown, i.e., the depth of soil d was derived:

$$\Delta\phi_i = 2\pi f t_i\left(\sqrt{K_{i+1}^2 + d^2} - \sqrt{K_i^2 + d^2}\right)/\sqrt{K_i^2 + d^2} \tag{7}$$

Equation (7) was numerically solved and the value of d was obtained. Most numerical methods need an upper and a lower bound to obtain an accurate estimate. In the calculation, a lower bound of 1 cm and an upper bound of 1 m were used, because a single layer of soil with uniform moisture distribution hardly ever spans the depth of one meter. Once dis estimated, the value of d was used in Eq. (6) to obtain the value of λ.

Finally, because that were R−1 adjacent antenna pairs, from Eqs (6) and (7), R−1 estimates of soil depth d and of signal wavelength A were obtained, and the averages were used to obtain final estimates of d and of λ.

Figure 8:
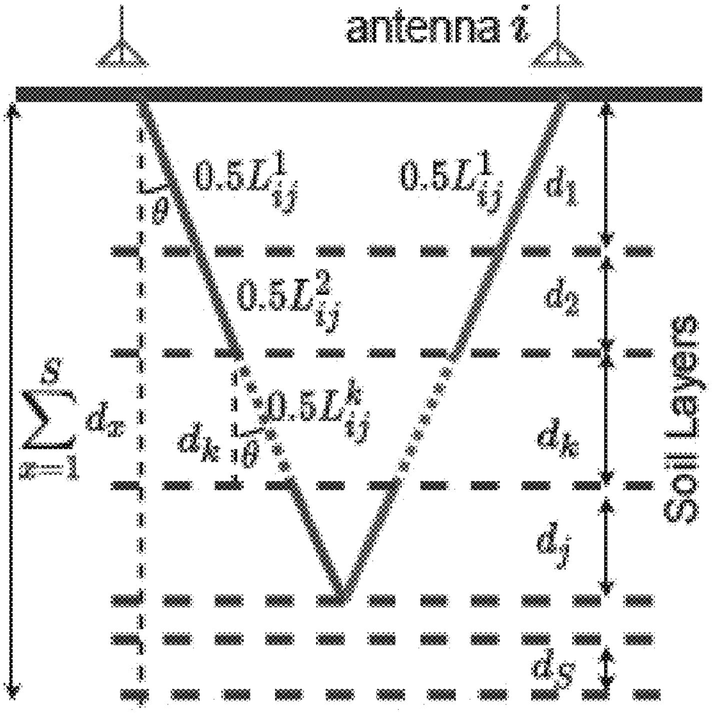
FIG. 8 is a diagram illustrating depth estimation, according to some implementations.

Estimation for Multiple Layers. In another example, the equations were generalized to handle the settings where the reflections arrive from multiple layers of soil. In this example, S denoted the total number of soil layers from which the antennas received reflections and the depth of the $j^{th}$ layer was denoted as $d_j$, where 1≤j≤S. It should be noted that the value S was equal to the number of peaks returned by the non-soil reflection filtering block. The total distance traversed by the reflection that arrives at the $i^{th}$ antenna after reflecting from the $j^{th}$ layer was represented by $L_{ij}$, where 1≤ i≤ R and 1≤j≤S. The distance traversed through the $k^{th}$ layer of soil by the reflection that arrives at the $i^{th}$ antenna after reflecting from the $j^{th}$ layer was represented by $$L_{ij}^k,$$

where 1≤k≤j. Referring now to FIG. 8, $$L_{ij}^1$$

denotes the portion of $L_{ij}$ reflection that passes through the first layer, $$L_{ij}^2$$

denotes the portion of $L_{ij}$ that passes through the second, and so on.

Referring now to Eq. (5), the phase change, $\Delta\phi_i$, between two successive antennas, i and i+1, depended on $\Delta l_i$ as well as the wavelength λ of the signal in the soil layer. However, when the signal passed through multiple soil layers, Eq. (5) was not suitable because it relied on a single value of λ relating to one soil layer, whereas 1 should be different for each soil layer. Accordingly, $\lambda_j$ denotes the wavelength of the signal in the $j^{th}$ soil layer. The phase difference observed between two successive antennas i and i+1 for the signal that returns after reflecting from the $j^{th}$ layer was denoted as $\Delta\phi_{ij}$. The observed phase difference, $\Delta\phi_{ij}$, was the sum of the shift in phase introduced by each layer k, where 1≤ k≤j, where $$\Delta\phi_{ij}^k$$

denote the phase shift contributed by the $k^{th}$ layer to the total observed phase difference $\Delta\phi_{ij}$. Accordingly, $\Delta\phi_{ij}$ was expressed as the sum of its constituents as follows:

$$\Delta\phi_{ij} = \sum_{k=1}^{1}\Delta\phi_{ij}^k,\ \forall\ 1 \le i \le R,\ 1 \le j \le S$$

Recall that $$L_{ij}^k$$

denoted the component of $L_{ij}$ in the $k^{th}$ soil layer. Thus, $$L_{ij} = \sum_{k=1}^{j} L_{ij}^k,$$

analogously to the definitions of $\Delta\phi_{ij}$. Thus, $$\Delta\phi_{ij}^k = 2\pi\Delta L_{ij}^k / = \lambda_k,$$

where $$\Delta L_{ij}^k = L_{i+1,j}^k - L_{ij}^k.$$

Thus, $\Delta\phi_{ij}$ was expressed as:

$$\Delta\phi_{ij} = \sum_{k=1}^{j}\frac{2\pi\left(L_{i+1,j}^k - L_{ij}^k\right)}{\lambda_k} \tag{8}$$

To simplify this equation, consider the geometry in FIG. 8, such that for any k≤j, $$\cos(\theta) = 2d_k / L_{ij}^k.$$

Similarly, $$\cos(\theta) = 2\sum_{x=1}^{j} d_x / L_{ij}.$$

Equating the two expressions for cos(θ), $$L_{ij}^{k}$$

was expressed as follows:

$$L_{ij}^{k} = \frac{d_k L_{ij}}{\sum_{x=1}^{j} d_x} = \frac{2d_k}{\sum_{x=1}^{j} d_x}\sqrt{K_i^2 + \left(\sum_{x=1}^{j} d_x\right)^2} \tag{9}$$

Substituting $$L_{ij}^{k}$$

from the equation above into Eq. (8), the following expression for $\Delta\phi_{ij}$ emerges.

$$\Delta\phi_{ij} = \frac{\sqrt{K_{i+1}^2 + \left(\sum_{x=1}^{j} d_x\right)^2} - \sqrt{K_i^2 + \left(\sum_{x=1}^{j} d_x\right)^2}}{\sum_{x=1}^{j} d_x} \times \sum_{k=1}^{j} \frac{4\pi d_k}{\lambda_k} \tag{10}$$

Further, it was required to resolve $\lambda_k$ in terms of some known parameters, such that $T_{ij}$ denoted the ToF of the $j^{th}$ reflection arriving at the $i^{th}$ antenna. Recall the value of each $T_{ij}$ was known from the PDP estimated at the $i^{th}$ antenna. The time the reflection from the $j^{th}$ soil layer arriving at the $i^{th}$ antenna spends in the $k^{th}$ soil layer was denoted as $$T_{ij}^{k},$$

where $$T_{ij}^{k} = T_{ik} - T_{i,k-1}$$

($T_{ik}$ and $T_{i,k-1}$ are similarly derived from PDPs). As $$\lambda_k = L_{ij}^{k} / f T_{ij}^{k},$$

it follows:

$$\lambda_k = \frac{\sqrt{K_i^2 + \left(\sum_{x=1}^{j} d_x\right)^2}}{\sum_{x=1}^{j} d_x} \times \frac{2d_k}{f T_{ij}^{k}} \tag{11}$$

Substituting $\lambda_k$ into Eq. (10):

$$\Delta\phi_{ij} = \frac{\sqrt{K_{i+1}^2 + \left(\sum_{x=1}^{j} d_x\right)^2} - \sqrt{K_i^2 + \left(\sum_{x=1}^{j} d_x\right)^2}}{\sqrt{K_i^2 + \left(\sum_{x=1}^{j} d_x\right)^2}} \times \sum_{k=1}^{j} 2\pi f T_{ij}^{k} \tag{12}$$

In Eq. (12), the only unknown was $$\sum_{x=1}^{j} d_x,$$

i.e., the depth beneath the soil surface from where the $j^{th}$ layer's reflection returned. To estimate $$\sum_{x=1}^{j} d_x$$

for all values of j, an iterative approach was taken. First, j=1 and R−1 estimates of $$\sum_{x=1}^{j} d_x$$

(corresponding to R−1 Rx antenna pairs) were obtained by numerically solving Eq. (12) averaging. When j=1, $$\sum_{x=1}^{j} d_x = d_1.$$

Thus, in the first iteration, the depth $d_1$ of the first layer was estimated. Generally, in the $j^{th}$ iteration, where $1<j\leq S$, Eq. (12) was solved numerically to estimate $$\sum_{x=1}^{j} d_x,$$

which gives the depth of the $j^{th}$ layer. Because the estimate of $$\sum_{x=1}^{j-1} d_x$$

was evaluated from the previous iteration, the vertical height of the $j^{th}$ layer as $$d_j = \sum_{x=1}^{j} d_x - \sum_{x=1}^{j-1} d_x$$

could be estimated.

Equation (10) was rearranged to obtain the values of $\lambda_j$, which resulted in the following expression for $\lambda_j$:

$$\lambda_j = \frac{4\pi d_j C_{ij}}{\sum_{x=1}^{j} d_x} \times \left(\Delta\phi_{ij} - \frac{C_{ij}}{\sum_{x=1}^{j} d_x} \sum_{k=1}^{j-1} \frac{4\pi d_k}{\lambda_k}\right)^{-1} \tag{13}$$

Where $$C_{ij} = \sqrt{K_{i+1}^2 + \left(\sum_{x=1}^{j} d_x\right)^2} - \sqrt{K_i^2 + \left(\sum_{x=1}^{j} d_x\right)^2}.$$

Again, setting j=1, the value of $\lambda_1$ was calculated using Eq. (10) in an iterative manner. More generally, in the $j^{th}$ iteration, where $1\leq j\leq S$, the wavelength of the signal in the $j^{th}$ soil layer was estimated by including the values of all $d_x$ that it estimated using Eq. (12) into Eq. (13), where $1 \leq x \leq j$. All $\lambda_k$ were calculated using Eq. (13) until the last iteration, where $k<j$.

Estimation with Antennas at a Height. In another example, the antennas are not placed on the soil surface by treating the air between the antennas and the soil surface as another layer. The depth of the air layer is denoted as $d_0$, which was equal to the distance between the antennas and the soil surface, which was known. Similarly, the wavelength of the signal when it passes through the air layer was denoted as $\lambda_0$ and is simply equal to c/f, where c is the speed of light in air. Therefore, air was treated as the first layer in the multi-layer measurement process described above, where the depth and wavelength parameters of this layer equal $d_0$ and $\lambda_0$, respectively, and are known apriori. Thus, now, j lies in the range [0, S], the smallest value that k can take on now is 0 instead of 1, and all the summation terms in Eqs. (12) and (13) start from 0 instead of 1. Again, the iterative measurement process was used here to calculate $d_j$ and $\lambda_j$ as used above.

Soil Moisture Estimation

Described herein are methods to determine the dielectric permittivity of each layer of soil and convert dielectric permittivity into soil moisture values, which is well known in the art.

Dielectric Permittivity. There are three different ways dielectric permittivity has been defined in prior literature: 1) absolute, 2) relative, and 3) apparent. Absolute dielectric permittivity, $\epsilon_o$, is the physical property of a material that quantifies how easily a material becomes polarized in the presence of an electric field [20]. Relative dielectric permittivity, $\epsilon_r$, is the ratio of the absolute dielectric permittivity of the material to that of the free space (i.e., $8.854\times10^{-12}$ F/m) [37]. While $\epsilon_r$ is a complex number, only its real component, i.e., $Re[\epsilon_r]$ is required to estimate the soil moisture content. Apparent dielectric permittivity, $\epsilon_p$, of a material is the permittivity that is measured through various properties of the material, such as the speed of signal when it passes through that material [29]. Under the assumption that the RF signal has a high enough frequency, the apparent permittivity is approximately equal to the real part of relative permittivity, i.e., $\epsilon_p \approx Re[\epsilon_r]$ [20].

The disclosed system and method operate in the frequency spectrum of 2 GHz to 3 GHz. Thus, the apparent permittivity estimate obtained from soil properties was used to estimate the soil moisture content. A relationship between wavelength and $\epsilon_p$ was derived to calculate $\epsilon_p$ using the estimated values of wavelengths. To derive this relationship, the speed of RF signal, v, in a medium was given by $v=c/\sqrt{\epsilon_p}$, where cis the speed of light and $\epsilon_p$ is the apparent dielectric permittivity of the medium [20]. As $v=f\lambda$, where $\lambda$ is the signal wavelength in the medium, then it follows:

$$\epsilon_p = \left(\frac{c}{f\lambda}\right)^2 \tag{14}$$

Recall that the value of $\lambda$ was previously estimated for each layer of soil, and thus, used Eq. (14) to estimate the apparent dielectric permittivity of each layer.

Soil Moisture. The soil moisture refers to the volumetric water content (VWC), $\psi$, which is the ratio of volume of water to the total soil+water volume. It is a unit-less quantity and is often expressed as percentage [39]. It is noted that as $\psi$ estimates the percentage of water in soil, it is an interval variable and not a ratio variable (see [6] for further details on differences between interval and ratio variables). The relationship between dielectric permittivity and VWC of soil is well documented in the literature. The Topp Equation [39], which relates VWC of soil with its apparent dielectric permittivity, was applied using the following equation.

$$\psi = 4.3\times10^{-6}\epsilon_p^3 - 5.5\times10^{-4}\epsilon_p^2 + 2.92\times10^{-2}\epsilon_p - 5.3\times10^{-2} \tag{15}$$

It is noted that several of the widely used contact-based soil moisture sensors also use this same Topp Equation to estimate VWC from the measured dielectric permittivity [7, 8].

Summary of Method Steps: First, the method included sweeping a signal from $f_s$=2 GHz to $f_e$=3 GHz in steps of $\delta f$=4 MHz; extracting all reflections; discarding any reflections that do not originate from any soil layer, as described above. The method further included applying the iterative method on the extracted reflections using Eqs. (12) and (13) to jointly estimate the depth of various soil layers as well as the wavelengths of the signal travelling through each of those layers, and estimating the permittivity of each soil layer using Eq. (14) followed by evaluating Eq. (15) to obtain the estimate of the VWC of each soil layer.

Figure 9:
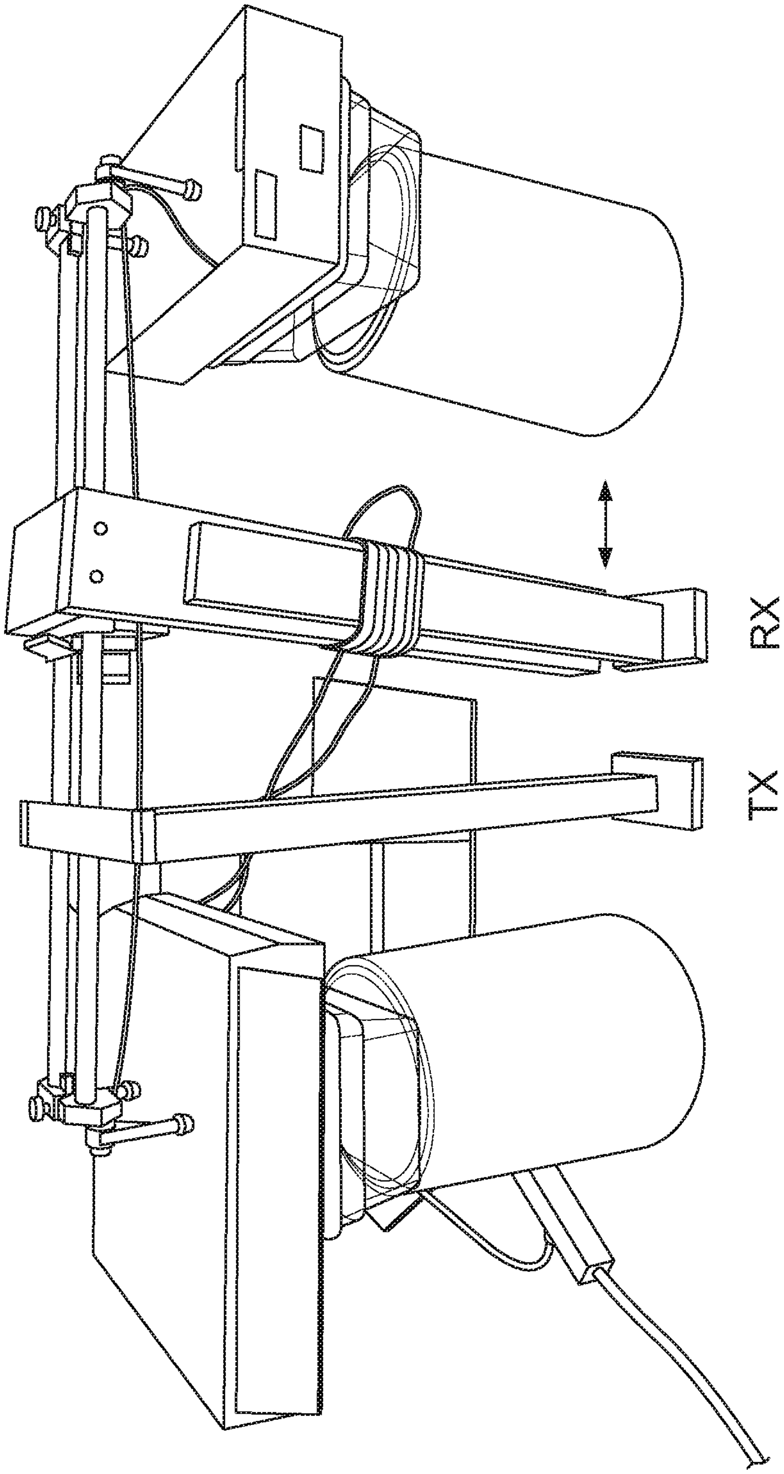
FIG. 9 is an image of an example configuration of the contactless moisture estimation system, according to some implementations.

Evaluation Setup. Software defined radio, X310 [9], was attached to a transmit and a receive antenna [10], each with a horizontal beamwidth of 66°. Referring now to FIG. 9, the transmit and receive antennas were placed side by side with a spacing of $\Delta tr$=10 cm between them and the antennas were at a certain height $d_0$ above the soil surface. In some examples, an optimum value of $d_0$ was found and used. To mimic a linear horizontal Rx antenna array, a slider [11] was programmed to move in steps of 2 cm, i.e., $\Delta r$=2 cm. The bidirectional arrow on the side of the receive antenna in FIG. 9 shows the direction of this antenna's motion. In the example shown in FIG. 9, the sliding antenna was used to mimic an array, which was used in lieu of an actual Rx antenna array, due to the high cost of additional software defined radios that were needed. It is noted that once such a system is implemented in production, the cost would be significantly low because the production system would be controlled by a custom ASIC instead of expensive software radios. To prevent direct signal leakage from transmit to receive antenna, a lossy foam absorber [12] was placed between the antennas to act as an RF shield.

To capture the reflections, the method further included sweeping the frequency from $f_s$=2 GHz to $f_e$=3 GHz in steps of $\delta f$=4 MHz with the receive antenna in its left most position. Next, the slider slides the receive antenna by 2 cm to the right, and again the frequency sweep was performed. This was repeated three more times, to mimic an Rx antenna array containing five antennas. Note that the total distance that the receive antenna moves is only 8 cm, which is two orders of magnitude smaller compared to the antenna offsets of up to 16.5 m that prior approaches needed. A python script running on a Raspberry Pi 4 collected the received signal from the software defined radio and executed the steps to estimate soil moisture at multiple depths in real-time. The system takes ~6 seconds to collect a measurement at each antenna and ~0.2 seconds to perform the processing, resulting in a total time of ~30 seconds to estimate the soil moisture. However, for a production system that uses a five-element antenna array to simultaneously collect the measurements, the moisture estimation time will reduce to ~6 seconds.

Experiment Sites. The system was evaluated in both indoor and outdoor environments with five different soils. In indoor environments, three different types of soil were placed in plastic containers, varying compositions of clay, silt, and sand. For outdoor environments, soil moisture was measured at two locations, a house yard and an agricultural field, each of which had small vegetation covers, as shown in FIG. 9.

Ground Truth. The ground truth was estimated using Teros-10 soil moisture sensor [4]. It had two electrodes that go into the soil at the desired depth to measure soil moisture at that depth. A contact-based sensor, such as Teros-10, provided only point-measurements that reflect soil moisture content at the specific location where the sensor was installed. It was observed that even at the same depth, the ground truth soil moisture measurements vary depending on the location, which resulted in soil moisture measurements that varied from 3 to 3.4. Thus, instead of measuring soil moisture at a single location, it was measured at multiple nearby locations to obtain a representative ground truth soil moisture range.

Evaluation Metric. For all evaluations, volumetric water content (VWC) was measured, which is the percentage of water+sand mixture's volume that is contributed by water. The Teros sensor provided a range of ground truth estimates, whereas the disclosed system provided only one VWC estimate, which were compared with the limits of the ground truth range. Whether the VWC estimates were within the limits was a determinant of whether the estimate was correct. The minimum and maximum values were denoted as $$\psi^{gt}_{min}$$

and $$\psi^{gt}_{max},$$

respectively, of the ground truth VWC range, and $\psi^C$ denoted the VWC estimate. The absolute error was quantified in the VWC estimate (subsequently called VWC error) with respect to the ground truth range using the expression $$\max(0, \psi^C - \psi^{gt}_{max}) + \max(0, \psi^{gt}_{min} - \psi^C).$$

Note that as all $$\psi^C, \psi^{gt}_{min},$$

and $$\psi^{gt}_{max}$$

are expressed as percentages, the VWC error is also expressed as a percentage. In keeping with prior work [20, 41], it should be understood that the error was not quantified in relative terms with respect to ground truth by dividing the VWC error with mean or median of the ground truth range. This is because VWC was an interval variable. Dividing two VWC values does not have any meaningful physical interpretation, but rather would lead to ambiguous conclusions from experimental observations.

Overall Accuracy. To study the overall accuracy, six readings were collected from each of the three soil types in an indoor environment over multiple days and four readings from each of the two outdoor locations. In each measurement, the locations of transmit and receive antennas were randomly varied to ensure that the system and method are robust to antenna placements. Further, two measurements were collected with two different soil types each indoors and two measurements with a soil outdoors to assess the impact of surface moisture. Finally, twenty measurements were conducted to analyze the impact of distance between transmit and Rx antenna array and of the height of antennas above the surface. In total, fifty-two measurements were collected across the indoor and outdoor environments.

Figure 10:
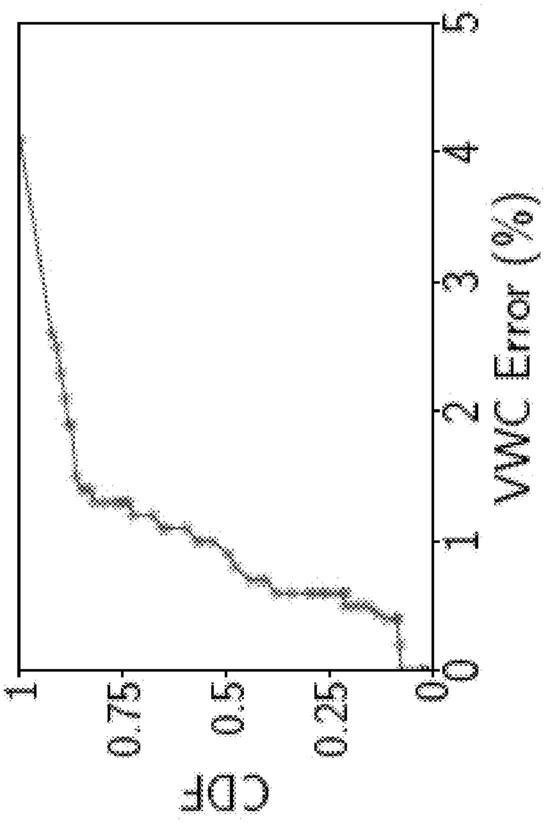
FIG. 10 is a graph illustrating results of CDF versus VWC Error, according to some implementations.

Referring now to FIG. 10, the CDF are shown from the estimates obtained across both indoor and outdoor environments from all the measurements listed above. FIG. 10 shows that the median and mean of VWC errors in estimates are only 0.9% and 0.7%, respectively. Even the maximum error was only 4.1%. The maximum depth from where reflections were received was 38 cm while median and mean depths were 22 cm and 21 cm, respectively. These observations show that the system and method can be used to estimate soil moisture in both indoor and outdoor environments with high accuracy.

In another example, a series of measurements were conducted over three consecutive days. Each day two measurements were collected from a soil contained in an indoor plastic container. The ground truth was measured using the Teros sensor immediately after taking each measurement using the disclosed system and method. Recall that when measuring the ground truth, values from twelve locations were collected in the container. After collecting the measurements on any given day, one liter of water was evenly poured on the soil to increase the amount of moisture in the soil and the next two measurements were taken after 24 hours to allow the water to seep throughout.

Figure 11:
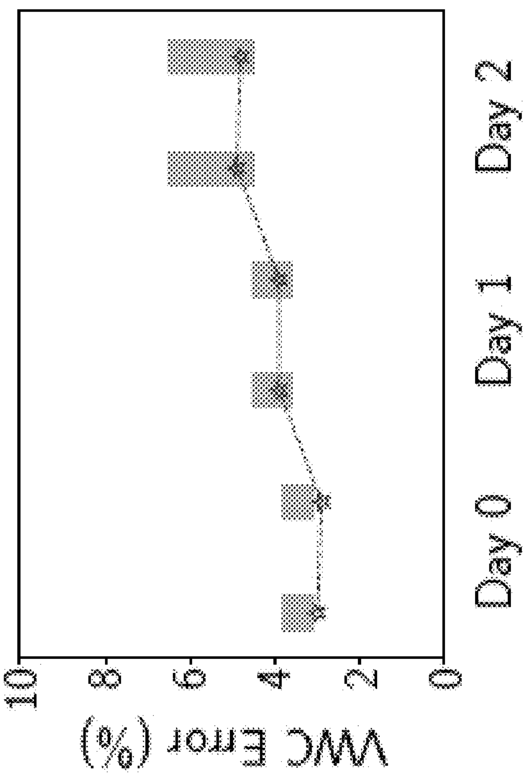
FIG. 11 is a graph illustrating results of a longitudinal evaluation, according to some implementations.

FIG. 11 shows the results from these experiments, wherein the dots and the line connecting them show the VWC estimated by the disclosed system and method while the vertical bars show the ground truth VWC ranges recorded by the Teros sensor. It is observed from FIG. 11 that the VWC values increased across days as water was added at the end of each day. It was also observed that the VWC estimates lied within the ground truth range for all measurements.

Figure 12:
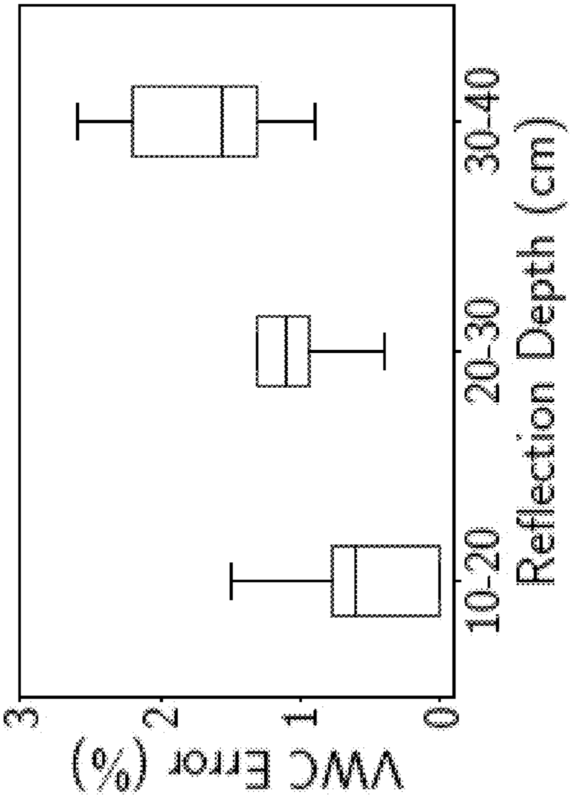
FIG. 12 is a graph illustrating results of evaluations of impact of depth, according to some implementations.

Impact of Soil Depth. In one example, the impact of soil depth on the accuracy of the estimates of the disclosed system and method was evaluated using the data from above. The disclosed system and method outputs multiple soil depths and one soil moisture estimate for each soil depth, and the ground truth values are measured from the corresponding depths. FIG. 12 plots the VWC error in the estimates at different depths and shows that as the soil depth increases, the absolute error in estimated VWC values also increases. Despite the increase in error with increase in depth, the median errors were 0.6% for 10-20 cm depth, 1.1% for 20-30 cm depth, and 1.5% for the 30-40 cm depth. In fact, even for the largest depth, more than 90% of estimates were within 2.7% of the ground truth range. Referring now to FIG. 10, the maximum value of VWC error is shown to be about 4% while in FIG. 12, it is 2.7%. This is because the tool used to draw the box plots in FIG. 12 eliminates outliers that constituted the tail of the CDF in FIG. 10.

Figure 13:
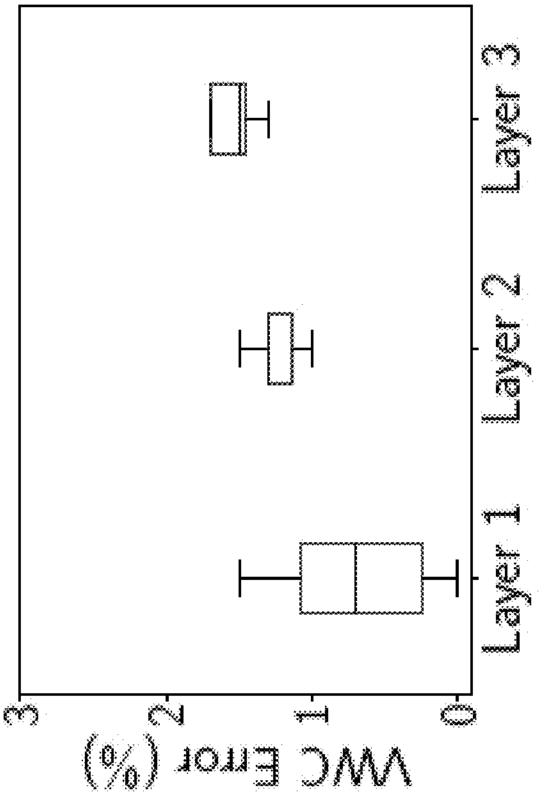
FIG. 13 is a graph illustrating results of evaluations of impact of soil layers, according to some implementations.

Impact of Soil Layers. To study the accuracy in estimating soil moisture for different layers, the estimates of the disclosed system and method were evaluated using the data from above and show the estimates from different layers separately. As shown in FIG. 13, each reflection was labelled with the depth from which it came and then all reflections were categorized into three groups (10-20 cm, 20-30 cm, and 30-40 cm). Each reflection was labeled with the layer number it corresponds to and then all reflections were categorized into three groups (Layer 1, Layer 2, and Layer 3). It was determined whether a reflection returned from the first, second, or third layer based on where the peak corresponding to that reflection lies in the PDP relative to other peaks. A reflection that is classified as Layer 1 belongs to the 20-30 cm depth group. FIG. 13 plots the VWC error in the estimates for different layers. It is noted that the error for the deeper soil layers is relatively higher compared to that for the upper layers, but still stays under 2%.

Figure 14:
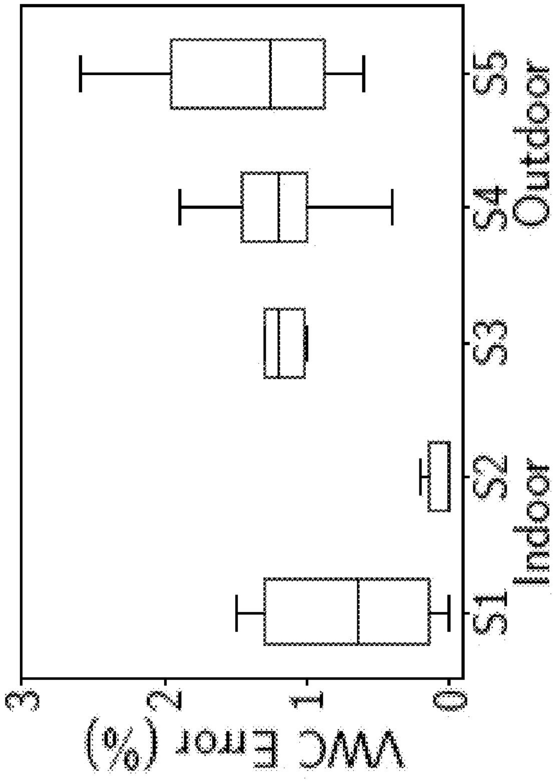
FIG. 14 is a graph illustrating results of evaluations of impact of soil type, according to some implementations.

Impact of Soil Type. To study accuracy across different soil types, six soil moisture readings were collected from each of the three indoor soil types, and four soil moisture readings were collected from each of the two outdoor soil types. Measurements were collected for three soil types labelled S1, S2, and S3 by placing them in plastic containers in indoor settings, while in outdoor settings, measurements were collected in a house yard (S4) and in an agricultural land (S5), both of which had some vegetation growth on them. FIG. 14 shows the VWC error for each soil type, and it is noted that the error is quite small across all soil types, where the median error lies in the range of just 0% for S2 soil to 1.3% for S5 soil. The three indoor soil types combined had a median error of 0.6% whereas the combined median error of the two outdoor environments was 1.3%. This shows that the disclosed system and method works well in both outdoor and indoor environments and is successfully able to eliminate the non-soil reflections.

Figure 15:
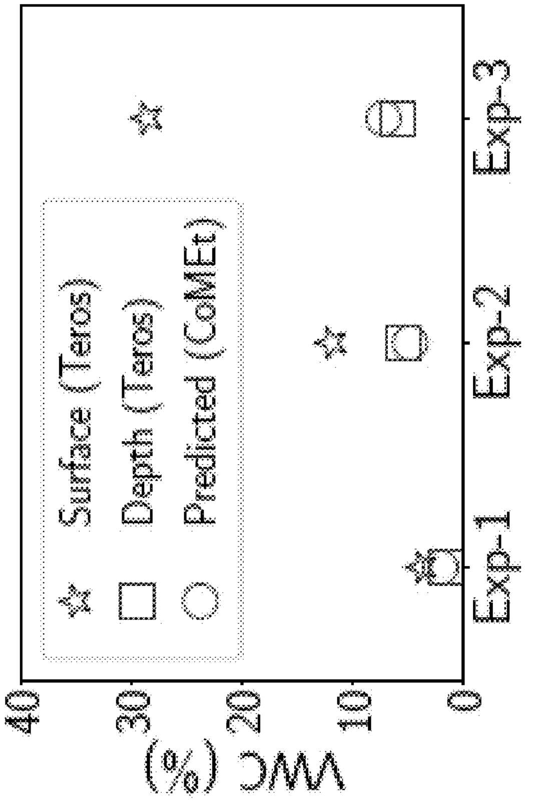
FIG. 15 is a graph illustrating results of evaluations of soil moisture, according to some implementations.

Impact of Surface Moisture. To evaluate the impact of surface moisture on soil moisture estimates, three experiments were conducted. The motivation behind conducting these experiments is that in settings such as soon after the rain, the surface moisture may be significantly higher than the soil moisture underneath, which can hinder the propagation of RF signals through the surface. Two experiments were conducted, Exp-1 and Exp-2, in indoor plastic containers where different amounts of water were poured into the samples and immediately measured the soil moisture afterwards using the disclosed system and method. A third experiment was conducted in the same way but outdoors, an hour after a rain. The ground truth values of VWC were measured at the surface as well as underneath using the Teros sensor. FIG. 15 shows the results from the three experiments. The star and square show the median VWC values measured using the Teros sensor at surface and underneath, respectively, whereas the circle shows the estimate obtained using the disclosed system and method (CoMEt). Recall that CoMEt provides estimates at multiple layers. The circles in this figure correspond to the estimates CoMEt provided for the layer where the ground truth was measured using the Teros sensor. In all these experiments, the VWC values estimated by CoMEt closely track the ground truth values despite the high value of surface moisture. This shows that CoMEt is as accurate as contact-based sensors despite high moisture content at the top. The reason is that as long as the signal is able to reach a certain layer underneath the surface, CoMEt's accuracy is not noticeably affected. The impact that higher moisture content at the surface can have, though, is that while the surface water has not yet seeped to the lower layers, the maximum depth at which CoMEt can estimate the moisture content can decrease.

Figure 16:
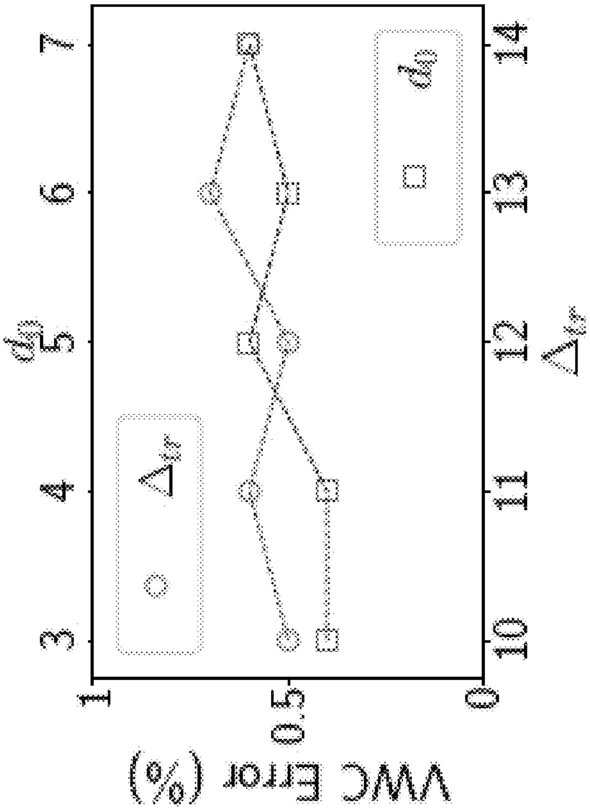
FIG. 16 is a graph illustrating results of evaluations of impact of Δtr and $d_0$, according to some implementations.

Impact of Design Parameters. Next, the impact of two design parameters was evaluated, namely the distance between the transmit antenna and the leftmost antenna in the Rx antenna array, i.e., Δtr, and the height of antennas above the soil surface, i.e., d0. To evaluate the impact of Δtr, measurements for Δtr=10 cm, 11 cm, 12 cm, 13 cm, and 14 cm were collected. For each value of Δtr, we collected two measurements were collected, the soil moisture was estimated using each of the two measurements, and then the average of the two VWC estimates was determined. Similarly, to evaluate the impact of $d_0$, it was varied from 3 cm to 7 cm in steps of 1 cm and two measurements were collected at each height. FIG. 16 shows the results from these experiments, where the bottom and top horizontal axes denote Δtr and $d_0$, respectively. Additionally, it is observed in FIG. 16 that the VWC error does not change appreciably with changes in either Δtr or $d_0$ and stays roughly the same at around 0.5%. However, if Δtr or $d_0$ are increased significantly, the error will increase. It is contemplated that at a limit of Δtr and $d_0$, the error will become increasing noticeably.

Figure 17:
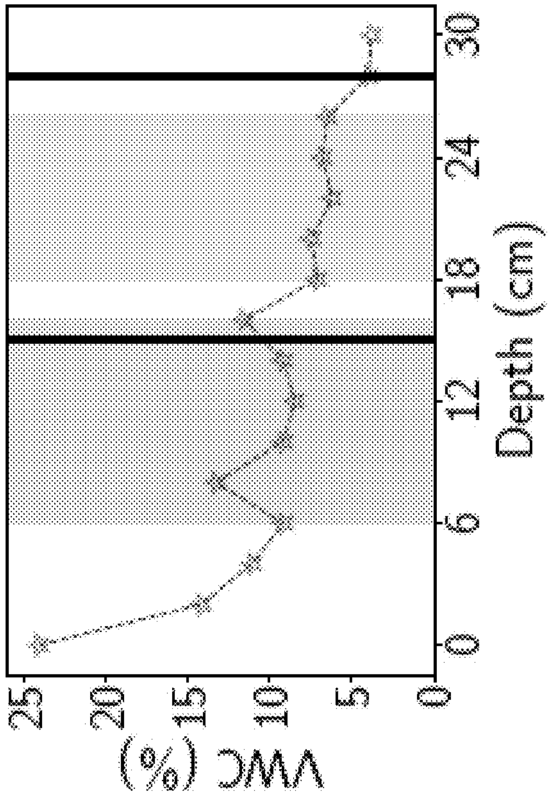
FIG. 17 is a graph illustrating results of evaluations of moisture versus to depth, according to some implementations.

Field Evaluations. This section includes a qualitative evaluation of how CoMEt measures soil moisture at multiple depths. To visualize the ground truth soil moisture at various depths, a borehole was dug to a depth of 30 cm in an outdoor setting, and then measure soil moisture using the Teros sensor at every 2 cm depth from the surface. Note that the electrodes of the sensor have been inserted sideways into the soil. FIG. 17 shows a plot of the measurements obtained by the Teros sensor with respect to the soil depth. From FIG. 17, three observations were made. First, the surface of the soil has a high moisture value of 24% that drops to 14% at 2 cm depth. Second, the soil moisture roughly stays the same between 6 cm and 16 cm at which point it drops considerably, stays roughly the same again between 18 cm and 26 cm, and then drops again. These two intervals are shaded in FIG. 17 at 6-16 cm and at 18-26 cm. In this environment, three soil reflections were received, first from near the surface, second from a depth of 15 cm, and third from the depth of 28 cm. The depths of second and the third reflections are shown with vertical lines in the figure, which lie very close to the two depths of significant moisture drop (i.e., 16 cm and 26 cm). Outlier behavior was observed at some points such as at depths of 8 cm and 16 cm, where the soil moisture rises. These sharp rises actually highlight the crucial limitation of contact-based sensors that if such sensors are not installed at representative locations, they may provide significantly inaccurate results.

Comparison with Prior Approaches. The disclosed system and method are herein compared to prior approaches. Strobe [20] reported the maximum VWC error of 3% compared to CoMEt's maximum error of 4.1%. Similarly, GreenTag [41] reported the 90th percentile error of 5% compared to CoMEt's 90th percentile error of 1.9%. Although the maximum error of CoMEt is slightly higher compared to Strobe's maximum error, it emphasizes the fundamental advantage that CoMEt has over Strobe, GreenTag, and all other prior approaches, i.e., CoMEt is contactless and can perform multi-depth measurements while Strobe and GreenTag are not contactless: Strobe places metallic rods while GreenTag places RFID tags under the soil. Even with the advantages that CoMEt has over prior approaches, its accuracy is still almost the same (and usually better) compared to the prior approaches.

Conclusion of Examples

The disclosed system and method (CoMEt) is an RF based contactless approach that measures soil moisture at multiple depths underneath the ground surface without installing any objects in the soil and without making any contact with the ground surface. The key technical novelty of CoMEt lies in leveraging the phase changes across successive antennas and the ToF of the received signal to jointly estimate soil depth and signal wavelength, and then using them to estimate soil moisture. The key technical solution of CoMEt lies in deriving theoretical relationships between phase changes, signal wavelengths, and depths of soil layers. These relationships were crucial to estimating dielectric permittivity of different soil layers and serve as a theoretical foundation for the future work on estimating moisture as well as other soil properties. CoMEt was evaluated in both indoor and outdoor environments with multiple types of soil and observed that CoMEt measured soil moisture for up to three layers of soil at the depth of up to 38 cm with median error of just 0.9%. With a more powerful signal, CoMEt should be able to measure the moisture at even greater depths.

Configuration of Certain Implementations

The construction and arrangement of the systems and methods as shown in the various implementations are illustrative only. Although only a few implementations have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative implementations. Other substitutions, modifications, changes, and omissions may be made in the design, operating conditions, and arrangement of the implementations without departing from the scope of the present disclosure.

The present disclosure contemplates methods, systems, and program products on any machine-readable media for accomplishing various operations. The implementation of the present disclosure may be implemented using existing computer processors, or by a special purpose computer processor for an appropriate system, incorporated for this or another purpose, or by a hardwired system. Implementations within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor.

When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

It is to be understood that the methods and systems are not limited to specific synthetic methods, specific components, or to particular compositions. It is also to be understood that the terminology used herein is for the purpose of describing particular implementations only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another implementation includes from the one particular value and/or to the other particular value. Similarly, when values are expressed as approximations, by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal implementation. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods.

Thus, if there are a variety of additional steps that can be performed it is understood that each of these additional steps can be performed with any specific implementation or combination of implementations of the disclosed methods.

Exemplary Aspects

Aspect 1. A system for contactless moisture estimation of soil, the system comprising: an antenna array comprising a first antenna configured to transmit radiofrequency (RF) signals and a plurality of second antennas configured to receive RF signals; and a controller electrically coupled to the antenna array, the controller configured to: emit, via the first antenna and into the soil, RF signals at each of a plurality of frequency increments (δf) ranging from a lower frequency (fs) to an upper frequency (fe); determine a channel frequency response (CFR) for each of the plurality of frequency increments (δf) by measuring an amplitude attenuation and a phase change of reflected RF signals detected by the plurality of second antennas; determine a power delay profile (PDP) for each of the plurality of second antennas based on the CFR of each of the plurality of frequency increments (δf); extract a subset of the reflected RF signals associated with the emitted RF signals by performing peak detection on the PDP of each of the plurality of second antennas; and for each layer of the soil and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

Aspect 2. The system of aspect 1, wherein lower frequency (fs) is 2 GHz and the upper frequency (fe) is 3 GHz.

Aspect 3. The system of aspect 1, the controller is further configured to filter out non-soil related reflections from the subset of the reflected RF signals by removing peaks that do not appear in the PDP of each of the plurality of second antennas.

Aspect 4. The system of aspect 3, wherein to filter out non-soil related reflections from the subset of the reflected RF signals, the controller is further configured to verify that a phase of the peaks detected in the PDP of each of the plurality of second antennas follow a linearly increasing pattern.

Aspect 5. The system of aspect 1, wherein the plurality of frequency increments (δf) are contiguous.

Aspect 6. The system of aspect 1, wherein the plurality of second antennas comprises at least three equidistantly spaced antennas.

Aspect 7. The system of aspect 1, wherein the estimated moisture content of each layer is estimated using a Topp equation.

Aspect 8. The system of aspect 1, wherein the controller comprises an RF generator to generate the RF signals.

Aspect 9. The system of aspect 8, wherein the RF generator is a software defined radio (SDR).

Aspect 10. The system of aspect 1, wherein the controller comprises a communications interface to communicate with a remote computing device.

Aspect 11. A method of contactless moisture estimation of soil, the method comprising: emitting, via a first antenna and into the soil, radiofrequency (RF) signals at each of a plurality of frequency increments (δf) ranging from a lower frequency (fs) to an upper frequency (fe); determining a channel frequency response (CFR) for each of the plurality of frequency increments (δf) by measuring an amplitude attenuation and a phase change of reflected RF signals detected by a plurality of second antennas; determining a power delay profile (PDP) for each of the plurality of second antennas based on the CFR of each of the plurality of frequency increments (δf); extracting a subset of the reflected RF signals associated with the emitted RF signals by performing peak detection of the PDP of each of the plurality of second antennas; and for each layer of the soil and for each of the subset of reflected RF signals, determining: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

Aspect 12. The method of aspect 11, wherein lower frequency (fs) is 2 GHz and the upper frequency (fe) is 3 GHz.

Aspect 13. The method of aspect 11, further comprising filtering out non-soil related reflections from the subset of the reflected RF signals by removing peaks that do not appear in the PDP of each of the plurality of second antennas.

Aspect 14. The method of aspect 13, wherein filtering out non-soil related reflections from the subset of the reflected RF signals further includes verifying that a phase of the peaks detected in the PDP of each of the plurality of second antennas follow a linearly increasing pattern.

Aspect 15. The method of aspect 11, wherein the plurality of frequency increments (δf) are contiguous.

Aspect 16. The method of aspect 11, wherein the plurality of second antennas comprises at least three equidistantly spaced antennas.

Aspect 17. The method of aspect 11, wherein the estimated moisture content of each layer is estimated using a Topp equation.

Aspect 18. A non-transitory computer readable medium having instructions stored thereon that, when executed by a computing device, cause the computing device to: operate a radiofrequency (RF) generator to emit, via a first antenna and into a medium, RF signals at each of a plurality of frequency increments (δf) ranging from a lower frequency (fs) to an upper frequency (fe); determine a channel frequency response (CFR) for each of the plurality of frequency increments (δf) by measuring an amplitude attenuation and a phase change of reflected RF signals detected by a plurality of second antennas; determine a power delay profile (PDP) for each of the plurality of second antennas based on the CFR of each of the plurality of frequency increments (δf); extract a subset of the reflected RF signals associated with the emitted RF signals by performing peak detection of the PDP of each of the plurality of second antennas; and for each layer of the medium and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

Aspect 19. The non-transitory computer readable medium of aspect 18, wherein lower frequency (fs) is 2 GHz and the upper frequency (fe) is 3 GHz.

Aspect 20. The non-transitory computer readable medium of aspect 18, further comprising filtering out non-medium related reflections from the subset of the reflected RF signals by removing peaks that do not appear in the PDP of each of the plurality of second antennas.

REFERENCES

[1] [n.d.]. https://www.epa.gov/watersense/statistics-and-facts.
[2] [n.d.]. https://gitfront.io/r/user-1279687/dfb6d2fb4bcc945dcdfdef117c9812d036682ac3/comet-moisture/.
[3] [n.d.]. https://www.onsetcomp.com/products/data-loggers-sensors/soil-moisture/.
[4] [n.d.]. https://www.metergroup.com/environment/products/teros-12/.
[5] [n.d.]. https://docs.scipy.org/doc/scipy/reference/generated/scipy. signal.find_peaks.html.
[6] [n.d.]. https://www.stat.purdue.edu/~tqin/system101/variable_type.pdf.
[7] [n.d.]. https://www.ictinternational.com/pdf/?product_id=255.
[8] [n.d.]. https://envcoglobal.com/files/docs/5te-manual-08.pdf.
[9] [n.d.]. https://kb.ettus.com/X300/X310.
[10] [n.d.]. https://www.alfa.com.tw/products/apa-m25.
[11] [n.d.]. https://www.amazon.com/Neewer-Centimeters-Stabilizer-Camcorder-Photography/dp/B06Y3MKC7C/.
[12] [n.d.]. http://www.masttechnologies.com/wp-content/uploads/2019/02/MF22-0009-00-Tech-Data-Sheet.pdf.
[13] [n.d.]. A Practical Guide for Installing and Interpreting Information from Soil Moisture Monitoring Technologies in Vineyards. https://www.vineyardteam.org/resources/resource-library/usingsoil-moisture-sensors-for-vineyard-irrigation-management.php.
[14] [n.d.]. Soil moisture monitoring: a selection guide. https://www.agric. wa.gov.au/horticulture/soil-moisture-monitoring-selection-guide.
[15] F Adib and et. al. 2014. 3D Tracking via Body Radio Reflections. In Usenix NSDI. USENIX Association, Seattle, WA, 317-329.
[16] J. H Bradford. 2008. Measuring water content heterogeneity using multifold GPR with reflection tomography. Vadose Zone Journal 7 (2008), 184-193. https://doi.org/10.2136/vzj2006.0160
[17] E. A Colman. 1946. The place of electrical soil-moisture meters in hydrologic research. Eos, Transactions American Geophysical Union. 27, 6 (1946), 847-853.
[18] M Cornick and et. al. 2016. Localizing Ground Penetrating RADAR: A Step Toward Robust Autonomous Ground Vehicle Localization. Field Robotics 33 (2016), 82-102. https://doi.org/10.1002/rob.21605
[19] A Dhekne and et. al. 2018. LiquID: A Wireless Liquid IDentifier. In MobiSys. Association for Computing Machinery, New York, NY, USA, 442-454. https://doi.org/10.1145/3210240.3210345
[20] J Ding and R Chandra. 2019. Towards Low Cost Soil Sensing Using Wi-Fi. In Mobicom. 1-16. https://doi.org/10.1145/3300061.3345440
[21] M. D Dukes. 2020. Two decades of smart irrigation controllers in US landscape irrigation. Transactions of the ASABE 63 (2020), 1593-1601, Issue 5.
[22] H Eller and A Denoth. 1996. A capacitive soil moisture sensor. Journal of Hydrology. 185, 1-4 (1996), 137-146. https://doi.org/10.1016/0022-1694(95)03003-4
[23] W Gardner and D Kirkham. 1952. Determination of soil moisture by neutron scattering. Social Science. 73, 5 (1952), 391-402.
[24] H Gerhards and et. al. 2008. Continuous and simultaneous measurement of reflector depth and average soil-water content with multichannel ground-penetrating radar. Geophysics 73 (2008), Issue 4. https://doi.org/10.1190/1.2943669
[25] M Gotcher and et. al. 2017. Smart Irrigation Technology: Controllers and Sensors. https://extension.okstate.edu/fact-sheets/smartirrigation-technology-controllers-and-sensors.html.
[26] G Griffiths-Sattenspiel and W Wilson. 2009. The Carbon Footprint of Water. https://www.csu.edu/cerc/researchreports/documents/CarbonFootprintofWater-RiverNetwork-2009.pdf.
[27] J. A Huisman and et. al. 2003. Measuring soil water content with ground penetrating radar: A review. Vadose Zone Journal 2 (2003), 476-491.
[28] F Jonard and et. al. 2012. Accounting for soil surface roughness in the inversion of ultrawideband off ground GPR signal for soil moisture retrieval. Geophysics 77 (2012). Issue 1. https://doi.org/10.1190/geo2011-0054.1
[29] G Kargas and et. al. 2020. The Effect of Soil Iron on the Estimation of Soil Water Content Using Dielectric Sensors. Water 12, 598 (2020).
[30] U. M Khan, R. H Venkatnarayan, and M Shahzad. 2020. RFMap: Generating Indoor Maps using RF Signals. In IPSN. 133-144. https://doi.org/10.1109/IPSN48710.2020.00-40
[31] A Klotzsche and et. al. 2018. Measuring Soil Water Content with Ground Penetrating Radar: A Decade of Progress. Vadose Zone Journal (2018). https://doi.org/10.1190/geo2011-0054.1
[32] S Lambot and et. al. 2004. Modeling of Ground-Penetrating Radar for Accurate Characterization of Subsurface Electric Properties. IEEE Transactions on Geoscience and Remote Sensing 42, 11 (2004).
[33] E Lee and S Kim. 2017. Pattern similarity based soil moisture analysis for three seasons on a steep hillslope. Journal of Hydrology 551 (2017), 484-494. https://doi.org/10.1016/j.jhydrol.2017.06.028
[34] B Levitas and et. al. 2011. UWB based oil quality detection. In ICUWB. IEEE, 220-224. https://doi.org/10.1109/ICUWB.2011.6058832
[35] L. A Richards. 1942. Soil moisture tensiometer materials and construction. Social Sci. 53, 4 (1942), 241-248.
[36] R Selmic and et. al. 2010. Ultra-wideband signal propagation experiments in liquid media. IEEE Transactions on Instrumentation and Measurement 59, 1 (2010).
[37] S Seybold, J. 2005. Introduction to RF Propagation. John Wiley & Sons. https://doi.org/10.1002/0471743690
[38] R Sui and J Baggard. 2015. Wireless Sensor Network for Monitoring Soil Moisture and Weather Conditions. Applied Engineering in Agriculture 31, 2 (2015), 193-200.
[39] G. C Topp, J. L Davis, and A. P Annan. 1980. Electromagnetic determination of soil water content: Measurements in coaxial transmission lines. Water Resources Research 16, 3 (1980).
[40] H Vereecken and et. al. 2007. Explaining soil moisture variability as a function of mean soil moisture: A stochastic unsaturated flow perspective. Geophysical Research Letters 34 (2007). Issue 22.
[41] J Wang and et. al. 2020. Soil Moisture Sensing with Commodity RFID Systems. In MobiSys. Association for Computing Machinery, New York, NY, USA, 273-285. https://doi.org/10.1145/3386901.3388940
[42] Q Wang and et. al. 2010. A novel soil measuring wireless sensor network. In IEEE Instrumentation Measurement Technology Conference Proceedings. IEEE, 412-415. https://doi.org/10.1109/IMTC.2010.5488224

[43] J Xiong and K Jamieson. 2013. ArrayTrack: A Fine-Grained Indoor Location System. Usenix NSDI (2013), 1-84.

[44] D Zhang and G Zhou. 2016. Estimation of Soil Moisture from Optical and Thermal Remote Sensing: A Review. Sensors. 16, 8 (2016). https://doi.org/10.3390/s16081308.

What is claimed is:

1. A system for contactless moisture estimation of soil, the system comprising:
- an antenna array comprising a first antenna configured to transmit radiofrequency (RF) signals and a plurality of second antennas configured to receive RF signals; and
- a controller electrically coupled to the antenna array, the controller configured to:
  - emit, via the first antenna and into the soil, RF signals at each of a plurality of frequency increments ($\delta_f$) ranging from a lower frequency ($f_s$) to an upper frequency ($f_e$);
  - determine a channel frequency response (CFR) for each of the plurality of frequency increments ($\delta_f$) by measuring an amplitude attenuation and a phase change of reflected RF signals detected by the plurality of second antennas, wherein the CFR for each of the plurality of frequency increments (δf) is in a frequency domain;
  - determine a power delay profile (PDP) for each of the plurality of second antennas based on the CFR of each of the plurality of frequency increments ($\delta_f$), wherein the PDP for each of the plurality of second antennas is determined by taking the CFR in the frequency domain for each frequency from $f_s$ to $f_e$ in increments of $\delta_f$, and then mapping the CFR in the frequency domain for each frequency from $f_s$ to $f_e$ to a time domain by taking an inverse fast Fourier transform (IFFT) of all $[(f_e-f_s)/\delta_f]+1$ CFR values;
  - extract a subset of the reflected RF signals associated with the emitted RF signals by performing peak detection on the PDP of each of the plurality of second antennas; and
  - for each layer of the soil and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

2. The system of claim 1, wherein lower frequency ($f_s$) is 2 GHz and the upper frequency ($f_e$) is 3 GHZ.

3. The system of claim 1, the controller is further configured to filter out non-soil related reflections from the subset of the reflected RF signals by removing peaks that do not appear in the PDP of each of the plurality of second antennas.

4. The system of claim 3, wherein to filter out non-soil related reflections from the subset of the reflected RF signals, the controller is further configured to verify that a phase of the peaks detected in the PDP of each of the plurality of second antennas follow a linearly increasing pattern.

5. The system of claim 1, wherein the plurality of frequency increments ($\delta_f$) are contiguous.

6. The system of claim 1, wherein the plurality of second antennas comprises at least three equidistantly spaced antennas.

7. The system of claim 1, wherein the estimated moisture content of each layer is estimated using a Topp equation.

8. The system of claim 1, wherein the controller comprises an RF generator to generate the RF signals.

9. The system of claim 8, wherein the RF generator is a software defined radio (SDR).

10. The system of claim 1, wherein the controller comprises a communications interface to communicate with a remote computing device.

11. A method of contactless moisture estimation of soil, the method comprising:
- emitting, via a first antenna and into the soil, radiofrequency (RF) signals at each of a plurality of frequency increments ($\delta_f$) ranging from a lower frequency ($f_s$) to an upper frequency ($f_e$);
- determining a channel frequency response (CFR) for each of the plurality of frequency increments ($\delta_f$) by measuring an amplitude attenuation and a phase change of reflected RF signals detected by a plurality of second antennas, wherein the CFR for each of the plurality of frequency increments ($\delta_f$) is in a frequency domain;
- determining a power delay profile (PDP) for each of the plurality of second antennas based on the CFR of each of the plurality of frequency increments ($\delta_f$), wherein the PDP for each of the plurality of second antennas is determined by taking the CFR in the frequency domain for each frequency from $f_s$ to $f_e$ in increments of $\delta_f$, and then mapping the CFR in the frequency domain for each frequency from $f_s$ to $f_e$ to a time domain by taking an inverse fast Fourier transform (IFFT) of all $[(f_e-f_s)/\delta_f]+1$ CFR values;
- extracting a subset of the reflected RF signals associated with the emitted RF signals by performing peak detection of the PDP of each of the plurality of second antennas; and
- for each layer of the soil and for each of the subset of reflected RF signals, determining: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

12. The method of claim 11, wherein lower frequency ($f_s$) is 2 GHz and the upper frequency ($f_e$) is 3 GHz.

13. The method of claim 11, further comprising filtering out non-soil related reflections from the subset of the reflected RF signals by removing peaks that do not appear in the PDP of each of the plurality of second antennas.

14. The method of claim 13, wherein filtering out non-soil related reflections from the subset of the reflected RF signals further includes verifying that a phase of the peaks detected in the PDP of each of the plurality of second antennas follow a linearly increasing pattern.

15. The method of claim 11, wherein the plurality of frequency increments ($\delta_f$) are contiguous.

16. The method of claim 11, wherein the plurality of second antennas comprises at least three equidistantly spaced antennas.

17. The method of claim 11, wherein the estimated moisture content of each layer is estimated using a Topp equation.

18. A non-transitory computer readable medium having instructions stored thereon that, when executed by a computing device, cause the computing device to:
- operate a radiofrequency (RF) generator to emit, via a first antenna and into a medium, RF signals at each of a plurality of frequency increments ($\delta_f$) ranging from a lower frequency ($f_s$) to an upper frequency ($f_e$);

determine a channel frequency response (CFR) for each of the plurality of frequency increments ($\delta_f$) by measuring an amplitude attenuation and a phase change of reflected RF signals detected by the plurality of second antennas, wherein the CFR for each of the plurality of frequency increments ($\delta_f$) is in a frequency domain;

determine a power delay profile (PDP) for each of the plurality of second antennas based on the CFR of each of the plurality of frequency increments ($\delta_f$), wherein the PDP for each of the plurality of second antennas is determined by taking the CFR in the frequency domain for each frequency from $f_s$ to $f_e$ in increments of $\delta_f$, and then mapping the CFR in the frequency domain for each frequency from $f_s$ to $f_e$ to a time domain by taking an inverse fast Fourier transform (IFFT) of all $[(f_e-f_s)/\delta_f]+1$ CFR values;

extract a subset of the reflected RF signals associated with the emitted RF signals by performing peak detection of the PDP of each of the plurality of second antennas; and for each layer of the medium and for each of the subset of reflected RF signals, determine: i) a wavelength of the reflected RF signal in a layer, ii) an estimated depth of the layer, iii) a dielectric permittivity of the layer based on the wavelength in the layer, and iv) an estimated moisture content of the layer based on the dielectric permittivity.

19. The non-transitory computer readable medium of claim 18, wherein lower frequency ($f_s$) is 2 GHz and the upper frequency ($f_e$) is 3 GHz.

20. The non-transitory computer readable medium of claim 18, further comprising filtering out non-medium related reflections from the subset of the reflected RF signals by removing peaks that do not appear in the PDP of each of the plurality of second antennas.

* * * * *